US006403314B1

(12) United States Patent
Lange et al.

(10) Patent No.: US 6,403,314 B1
(45) Date of Patent: Jun. 11, 2002

(54) COMPUTATIONAL METHOD AND SYSTEM FOR PREDICTING FRAGMENTED HYBRIDIZATION AND FOR IDENTIFYING POTENTIAL CROSS-HYBRIDIZATION

(75) Inventors: Daniel H. Lange, Kfar Vradim (IL); Nicholas M. Sampas, San Jose; Paul K. Wolber, Los Altos, both of CA (US); Zohar H. Yakhini, Zikhron Ya'acov (IL)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/498,608

(22) Filed: Feb. 4, 2000

(51) Int. Cl.[7] .................... C12Q 1/68; C12P 19/34; G01N 33/48
(52) U.S. Cl. .................... 435/6; 435/91.2; 702/19; 702/20; 536/22.1
(58) Field of Search .................... 702/14, 20; 435/6, 435/91.2; 536/22.1

(56) References Cited

U.S. PATENT DOCUMENTS

| 5,856,103 A | * | 1/1999 | Gray et al. ................. 435/6 |
| 5,873,052 A | * | 2/1999 | Sharaf ......................... 702/20 |

* cited by examiner

*Primary Examiner*—Jeffrey Fredman

(57) ABSTRACT

A computational method and system for predicting the hybridization potential for two polymers. A probe/target interaction matrix is prepared to contain indications of all possible probe/target subunit interaction stabilities. The probe/target interaction matrix is analyzed to create a list of possible single-fragment hybridizations. A graph is then generated with vertices representing fragments, and edges representing possible loops in one or both of the probe and target sequences that allow the pair of fragments interconnected by the edge to coexist within a multi-fragment cross-hybridization. Finally, the graph is analyzed to construct a list of all possible single-fragment and multi-fragment cross-hybridizations possible between the probe molecule and the target molecule. The different hybridizations are scored and sorted by score.

52 Claims, 8 Drawing Sheets

COMPUTATIONAL METHOD AND SYSTEM FOR PREDICTING FRAGMENTED HYBRIDIZATION AND FOR IDENTIFYING POTENTIAL CROSS-HYBRIDIZATION

TECHNICAL FIELD

The present invention relates to computational methodologies for designing hybridization assays, polymerase chain reaction amplifications, and anti-sense drugs and, in particular, to a computational method and system for predicting the hybridization potential of a probe molecule/target molecule pair.

BACKGROUND OF THE INVENTION

The present invention relates to computationally predicting the stability of non-covalent binding between a probe molecule and a target molecule. The current application will specifically address hybridization of deoxyribonucleic acid ("DNA") polymers, although the techniques and methodologies described in the current application may be applied to DNA and ribonucleic acid ("RNA") hybridization, RNA/RNA hybridization, hybridization of various synthetic polymers, and hybridization of other types of polymer molecules.

DNA molecules are linear polymers, synthesized from only four different types of subunit molecules: (1) deoxyadenosine, abbreviated "A," a purine nucleoside; (2) deoxythymidine, abbreviated "T," a pyrimidine nucleoside; (3) deoxy-cytosine, abbreviated "C," a pyrimidine nucleoside; and (4) deoxy-guanosine, abbreviated "G," a purine nucleoside. FIG. 1 illustrates a short DNA polymer 100, called an oligomer, composed of the following subunits: (1) deoxyadenosine 102; (2) deoxy-thymidine 104; (3) deoxycytosine 106; and (4) deoxy-guanosine 108. When phosphorylated, subunits of the DNA molecule are called nucleotides, and are linked together through phosphodiester bonds 110–115 to form the DNA polymer. A linear DNA, such as the oligomer shown in FIG. 1, molecule has a 5' end 118 and a 3' end 120. A DNA polymer can be chemically characterized by writing, in sequence from the 5' end to the 3' end, the single letter abbreviations for the nucleotide subunits that together compose the DNA polymer. For example, the oligomer 100 shown in FIG. 1 can be chemically represented as "ATCG." A nucleotide comprises a purine or pyrimidine base (e.g. adenine 122 of the deoxyadenylate nucleotide 102), a deoxy-ribose sugar (e.g. ribose 124 of the deoxy-adenylate nucleotide 102), and a phosphate group (e.g. phosphate 126) that links the nucleotide to the next nucleotide in the DNA polymer. RNA polymers are similar to DNA polymers, except that 2'-hydrogens, such as 2'-hydrogens 126, are replaced with hydroxyl groups and the pyrimidine uridine replaces the pyrimidine thymine, where the 5'-methyl group of thymine is replaced by a hydrogen in uridine.

The DNA polymers that contain the organizational information for living organisms occur in the nuclei of cells in pairs, forming double-stranded DNA helices. One polymer of the pair is laid out in a 5' to 3' direction, and the other polymer of the pair is laid out in a 3' to 5' direction. The two DNA polymers in a double-stranded DNA helix are therefore described as being anti-parallel. The two DNA polymers, or strands, within a double-stranded DNA helix are bound to each other through attractive forces including hydrophobic interactions between stacked purine and pyrimidine bases and hydrogen bonding between purine and pyrimidine bases, the attractive forces emphasized by conformational constraints of DNA polymers. Because of a number of chemical and topographic constraints, double-stranded DNA helices are most stable when deoxy-adenylate subunits of one strand hydrogen bond to deoxy-thymidylate subunits of the other strand, and deoxy-guanylate subunits of one strand hydrogen bond to a deoxy-cytidylate subunits of the other strand.

FIGS. 2A–B illustrate the hydrogen bonding between purine/pyrimidine base pairs of two anti-parallel DNA strands. FIG. 2A shows hydrogen bonding between an adenine and a thymine, and FIG. 2B shows hydrogen bonding between a guanine and a cytosine. Note that there are two hydrogen bonds 202 and 203 in the adenine/thymine base pair, and three hydrogen bonds 204–206 in the guanine/cytosine base pair, as a result of which GC base pairs contribute greater thermodynamic stability to DNA duplexes than AT base pairs. AT and GC base pairs, illustrated in FIGS. 2A–B, are known as Watson-Crick ("WC") base pairs.

Two DNA strands linked together by hydrogen bonds form the familiar helix structure of a double-stranded DNA helix. FIG. 3 illustrates a short section of a DNA double helix 300 comprising a first strand 302 and a second, anti-parallel strand 304. The ribbon-like strands in FIG. 3 represent the deoxyribose and phosphate backbones of the two anti-parallel strands, with hydrogen-bonded purine and pyrimidine base pairs, such as base pair 306, interconnecting the two strands. Deoxy-guanylate subunits in one strand are generally paired with deoxy-cytidylate subunits in the other strand, and deoxy-thymidylate subunits in one strand are generally paired with deoxy-adenylate subunits in the other strand. However, non-WC base pairings may occur within double-stranded DNA. Generally, purine/pyrimidine non-WC base pairings contribute little to the thermodynamic stability of a DNA duplex, but generally do not destabilize a duplex otherwise stabilized by WC base pairs. Such base pairs are referred to below as "non-WC" base pairs. However, purine/purine base pairs may destabilize DNA duplexes, as may, to a lesser extent, pyrimidine/pyrimidine base pairs. Such base pairings are referred to below as "anti-WC" base pairs.

Double-stranded DNA may be denatured, or converted into single-stranded DNA, by changing the ionic strength of the solution containing the double-stranded DNA or by raising the temperature of the solution. Single-stranded DNA polymers may be renatured, or converted back into DNA duplexes, by reversing the denaturing conditions, for example by lowering the temperature of the solution containing the single-stranded DNA polymers. During the renaturing process, complementary bases of anti-parallel strands form WC base pairs in a cooperative fashion, leading to regions of DNA duplex. However, many different types of associations between and within DNA polymers may occur that may lead to many different types of mismatching between single strands of DNA. In general, the longer the regions of consecutive WC base pairing between two single strands of DNA, the greater the stability of hybridization of the two polymers under renaturing conditions.

The ability to denature and re-nature double-stranded DNA has led to development of many extremely powerful and discriminating assay technologies for identifying the presence of single-stranded or double-stranded DNA of particular base sequences or containing particular subsequences within complex mixtures of different DNA polymers and other bio-polymers and chemical substances. These methodologies include the polymerase chain reaction ("PCR"), molecular-array-based hybridization assays, fluorescent in situ hybridization ("FISH"), and anti-sense nucleic acid bio-polymers that may be used as therapeutic agents or research tools to block expression of particular genes within an organism. FIG. 4 illustrates probe/target hybridization that underlies hybridization assays. A probe 402 is synthesized to contain a short single-stranded DNA of a particular sequence 404 attached to a second chemical entity 406 represented in FIG. 4 as an unfilled disk. The nature of the second chemical entity 406 varies depending on the technique in which the probe is employed. The probe is brought into contact with a solution of single-stranded DNA polymers 408–412 having different sequences. The solution is then modified to become a renaturing environment, for example by changing the ionic strength of the solution or lowering the temperature of the solution, to allow for hybridization of the single-stranded-DNA portion of the probe molecules 404 with single-stranded DNA molecules having complementary sequences 410. Thus, a probe molecule, in figurative terms, fishes out a single-stranded DNA polymer having a complementary or near-complementary sequence from a complex solution of DNA molecules having non-complementary sequences and perhaps other chemical entities, such as other biopolymers and organic compounds.

In molecular-array-based hybridization assays, the DNA polymer portion 404 of a probe is covalently attached to a solid substrate 406. Probes having different DNA sequences are synthesized on different regions of the surface of the substrate. The single-stranded DNAs that hybridize to the substrate-bound probe molecules are chemically modified to contain fluorophores, chemophores, or radioisotopes. Following hybridization of the modified single-stranded DNA polymers to probes, the unhybridized single-stranded DNA polymers are washed from the surface of the molecular array, and bound sample DNA polymers are detected by spectroscopy or radiography. Using molecular-array-based assays, many hundreds or thousands of different types of probes having different, known DNA sequences can be concurrently employed to hybridize to sample DNA molecules to detect and quantify the presence of DNA polymers containing sequences complementary to the probe sequences in fantastically complex solutions of DNA polymers generated, for example, by extracting active messenger RNA ("mRNA") from cells of living organisms.

In the FISH technique, a probe contains an oligonucleotide having a specific sequence 404 bound to a fluorophore 406. The probes are introduced into a biological sample under renaturing conditions and then detected via fluoroscopy, allowing the locations of DNA polymers having subsequences complementary to the probe sequence to be visualized. In the PCR technique, oligonucleotides with specific sequences are hybridized to single-stranded DNA and the oligonucleotides are synthetically extended via the DNA polymerase reaction. Many cycles of the PCR technique are used to amplify DNA sequences flanked by contiguous sequences complementary to the oligonucleotide primer. Anti-sense drugs are DNA or RNA polymers with specific sequences designed to bind to complementary sequences within an organism's DNA or mRNA in order to block expression of genes containing the sequences or controlled by control regions containing the sequences.

While hybridization assays and techniques such as PCR and anti-sense drugs have the potential for exquisite discrimination and selectivity in hybridizing probe DNA sequences to target complimentary subsequences of single-stranded DNAs, there is also a large potential for unwanted and less discriminating hybridization that can greatly decrease the selectivity and discrimination of a particular assay. FIGS. 5A–C illustrate various types of undesirable cross-hybridization reactions between probe molecules and sample molecules that can decrease the selectivity and signal-to-noise ratio of hybridization assays and decrease the selectivity of PCR and anti-sense methodologies. Hybridization of a subsequence of the probe oligonucleotide sequence with a complimentary subsequence of a sample DNA polymer is illustrated in FIG. 5A. The probe 502 in FIG. 5A is synthesized to hybridize with, and select sample molecules containing, the subsequence TCGCTACGGAT. However, as shown in FIG. 5A, a sample molecule 504 containing the subsequence CGCTA 506 hybridizes to the complimentary subsequence TAGCG 508 of the probe molecule. Thus, the probe has hybridized with a sample molecule that does not contain a full complimentary sequence to the oligonucleotide sequence of the probe molecule. Such subsequence hybridization greatly diminishes the selectivity of the probe for particular sequences. In the current example, the 11-subunit sequence of the probe is one out of $4^{11}$ possible 11-subunit oligonucleotide sequences, whereas the subsequence TAGCG is merely one out of $4^5$ possible 5-subunit oligonucleotide sequences. Obviously, 1 out of $4^{11}$ represents far greater selectivity than 1 out of $4^5$. Thus, in addition to target single-stranded DNAs containing the full complimentary sequence TCGATACGGAT, many unwanted sample DNA polymers containing the complementary subsequence CGCTA, and many other subsequences of the probe oligonucleotide sequence, may hybridize to probe molecules having the sequence ATCCGTAGCGA. In the following, a single stretch of consecutive WC base pairings between probe and target molecules that does not encompass the entire probe sequence is referred to as a "fragment."

In addition to subsequence cross-hybridization illustrated in FIG. 5A, various types of fragmented cross-hybridizations are possible. FIG. 5B illustrates an omega two-fragment cross-hybridization. In FIG. 5B, a first subsequence of an unwanted sample molecule 510 having the sequence TCGC is hybridized to the terminal subsequence 512 GCGA of the probe molecule, and a second subsequence 514 GGAT of the unwanted sample DNA polymer has hybridized to the initial subsequence 516 ATCC of the probe molecule. The two hybridizing subsequences 510 and 514 of the unwanted sample DNA molecule are separated by a loop 518 of DNA.

FIG. 5C illustrates a two-fragment delta cross-hybridization. The unwanted sample DNA 520 in FIG. 5C has the same two complementary subsequences 522 and 524 as subsequences 510 and 514 of unwanted sample DNA polymer 518 in FIG. 5B, hybridized to the same probe subsequences 526 and 528 as unwanted sample DNA molecule 518 hybridized to in FIG. 5B. However, the orientations of the unwanted sample DNA subsequences 522 and 524 are opposite to the orientations of the subsequences 510 and 514, respectively, in unwanted sample DNA molecule 518 of FIG. 5B. Hybrid cross-hybridizations and cross-hybridizations comprising more than two fragments are also possible.

In order to prevent cross-hybridizations in hybridization-based assays, in the PCR technique, and in designing anti-sense polymers, researchers and manufacturers strive to create probe molecules containing oligonucleotide sequences with high specificity for particular target molecules and with low cross-hybridization potential for other non-target polymers that may be present in the samples to which the probe molecules are exposed. The problem of identifying desirable probe molecules is not trivial. The potential for cross-hybridization of a given probe molecule with hundreds, thousands, or tens of thousands of potential non-target DNA polymers presents an extremely computationally intensive task. To date, because of the combinatorial explosion involved in identifying cross-hybridization potentials, computational methodologies for evaluating cross-hybridization potentials of probe molecules have focused primarily on cross-hybridization between an entire probe molecule and complementary and closely mismatched regions of target molecules. In this approach, a certain degree of consideration is implicitly given to subsequence hybridization, illustrated in FIG. 5A. However, because of failing to take into account fragmented cross-hybridization, illustrated in FIGS. 5B–C, current and prior art computational techniques may select probe molecule candidates with undesirable cross-hybridization potentials for unwanted non-target sequences. Therefore, researchers, developers, and manufacturers of hybridization-based methodologies and techniques have recognized the need for computational techniques for evaluating cross-hybridization potentials of probe molecules that take into account fragment cross-hybridization, as illustrated in FIGS. 5B and 5C, as well as hybrid and multi-fragment hybridization.

SUMMARY OF THE INVENTION

The present invention provides a computational method for determining the hybridization potential of a probe molecule with a target molecule. The hybridization potential includes the potential of the probe molecule to completely hybridize with a complementary subsequence within the target molecule, as well as the potential for single-fragment and multi-fragment subsequence cross-hybridization. First, a probe/target interaction matrix is prepared to contain indications of all possible probe/target subunit interaction stabilities. Next, the probe/target interaction matrix is analyzed to create a list of all possible single-fragment hybridizations as well as hybridization of the entire probe sequence with one or more complementary subsequences of the target molecule, when possible. Next, a graph is generated with vertices representing individual fragments found in the previous step, and edges representing possible loops in one or both of the probe and target sequences that allow the pair of fragments interconnected by the edge to coexist within a multi-fragment cross-hybridization. Finally, the graph is analyzed to construct a list of all possible single-fragment and multi-fragment cross-hybridizations possible between the probe molecule and the target molecule. A score representing the overall stability of hybridization, based on the total length of complementary fragments or based on a thermodynamic calculation, is calculated for each single-fragment and multi-fragment cross-hybridization in the list of cross-hybridizations, and the list may be sorted based on the calculated scores to produce a sorted sublist representing the most stable potential single-fragment and multi-fragment cross-hybridizations that may occur between the probe molecule and the target molecule. The method may be iteratively applied to a large number of probe/sample molecule pairs in order to select probe molecules that have high hybridization potentials for desired target molecules that have low hybridization potentials for any other sample molecules to which the probe may be exposed during an assay, when used as a primer, or initiator sequence, in PCR, or when used as an anti-sense compound.

DETAILED DESCRIPTION OF THE INVENTION

The present invention relates to the computation of the hybridization potential of a probe polymer molecule with a target polymer molecule. The present invention is described, below, using examples in which both the probe and target molecules are DNA polymers. However, the present invention may be applied to hybridization between other types of biopolymers and synthetic polymers that hybridize as a result of subunit interactions, including DNA/RNA hybridization and RNA/RNA hybridization. The present invention is described, below, in two subsections. In the first subsection, a high-level pseudo-code description of the invention is provided with reference to FIGS. 4–13. In the second subsection, an alternative C++-like pseudo-code embodiment is provided along with results generated from an exemplary probe and target pair. As with most computational techniques and methodologies, an almost limitless number of alternative embodiments might be provided for the present invention. Different ordering of steps, different modular organizations within the program implementing the present invention, different numbers and types of variables and data structures, different inputs and outputs, and different control structures may be combined to produce an almost limitless number of different programs that implement the present invention. The two pseudo-code implementations provided below provide a detailed illustration of the present invention, but are not intended to in any way to limit the scope of the claims that follow.

High-Level Pseudo-Code Description

In this subsection, a high-level pseudo-code implementation of one embodiment of the present invention is provided with references to FIGS. 6–13 that illustrate various aspects of the structure and operation of the pseudo-code implementation. Input to the program that represents one embodiment of the present invention is described below:

```
1    Input:
2
3    ProbeSeq    -the probe sequence, length = lp.
4    TarSeq      -the target sequence, length = lt.
5    Stab        -matrix containing stability values for pairs of
6                nucleotides. In the symbolic case, 1 for WC
7                complements, 0 for others. In the thermodynamic
                 case, as dictated by the model.
8    σ           -a stability threshold for single fragments, equal to the
9                length of the fragment, in the symbolic case.
```

Figure 1:
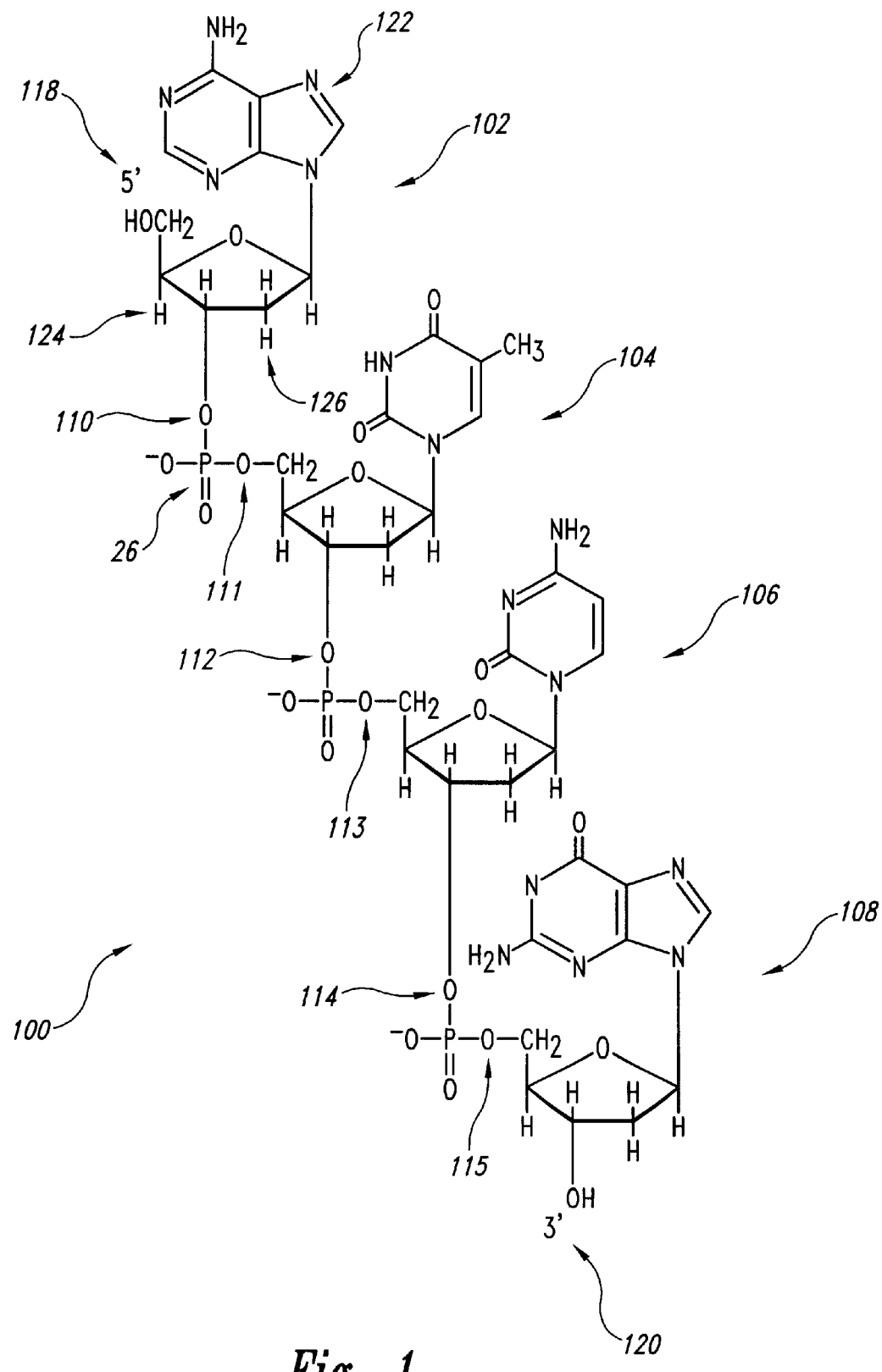
FIG. 1 shows a 4-nucleoside DNA oligomer having the subunit sequence "ATCG."
Figure 2A:
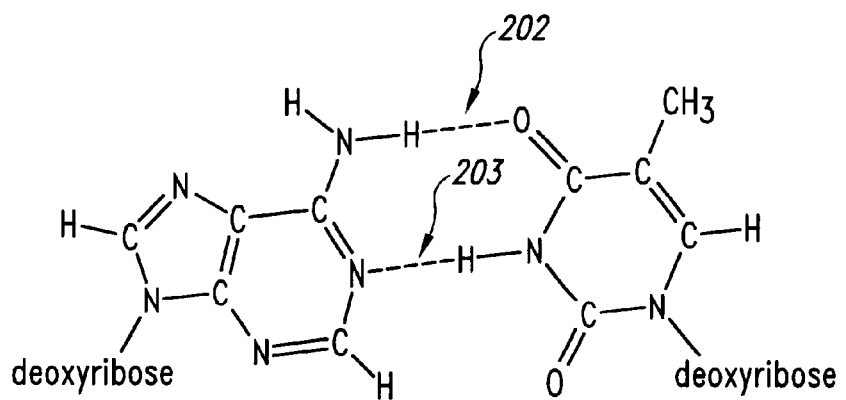
FIGS. 2A–B illustrate the hydrogen bonding between purine/pyrimidine base pairs of two anti-parallel DNA strands.
Figure 2B:
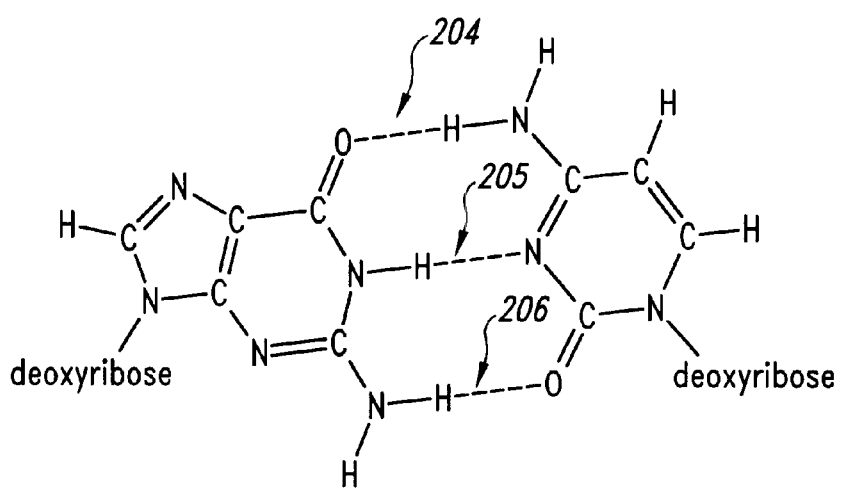
Figure 3:
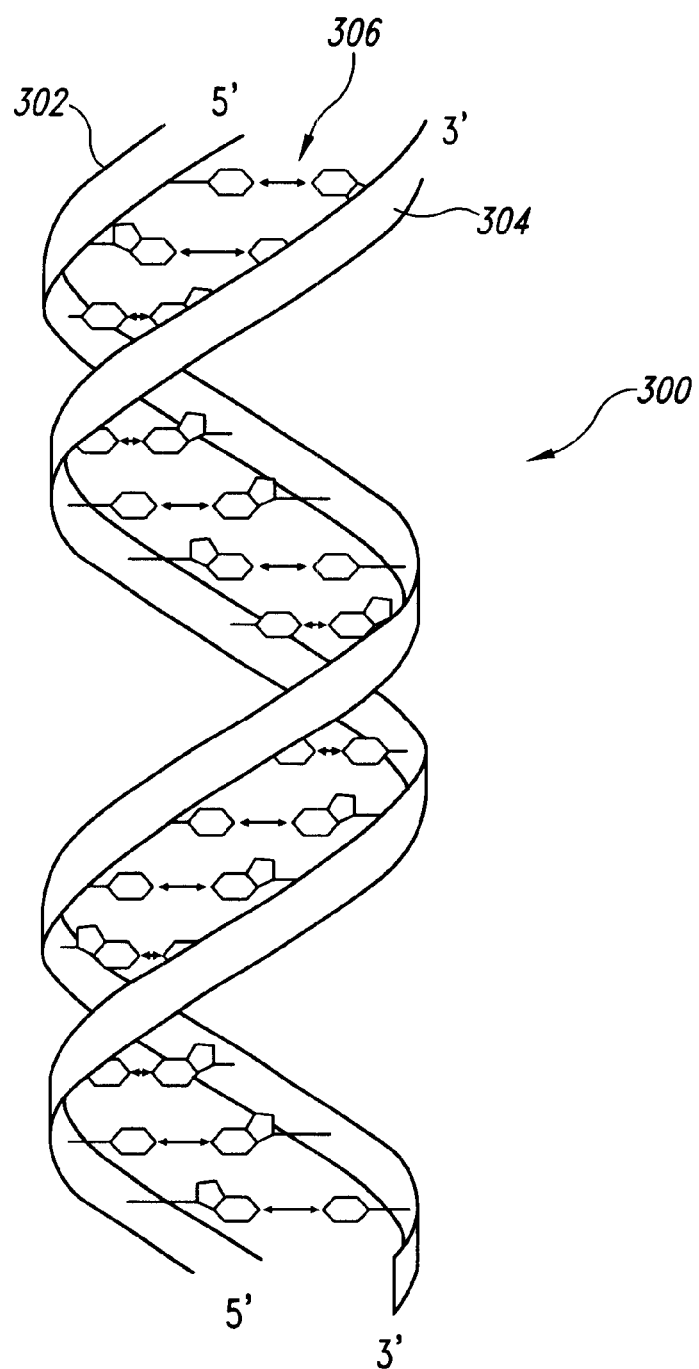
FIG. 3 illustrates a short section of a DNA double helix comprising a first DNA strand and a second, anti-parallel DNA strand.
Figure 4:
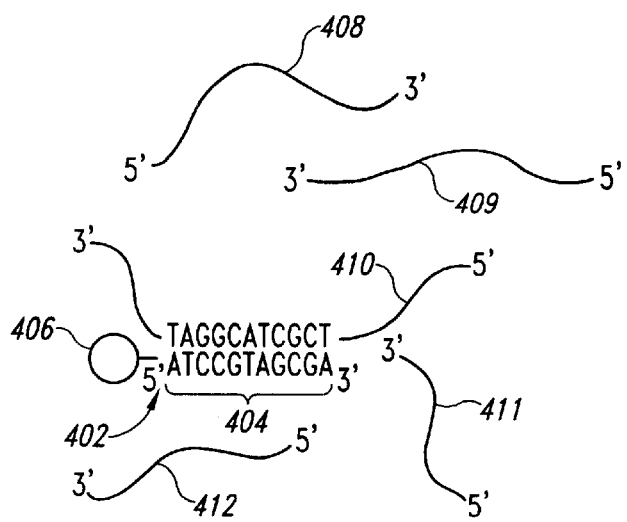
FIG. 4 illustrates probe/target hybridization that underlies hybridization assays.
Figure 5A:
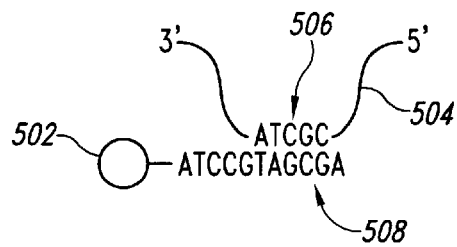
FIGS. 5A–C illustrate various types of undesirable cross-hybridization reactions between probe molecules and sample molecules that can decrease the sensitivity and signal-to-noise ratio of hybridization assays and decrease the selectivity of PCR and anti-sense methodologies.
Figure 5B:
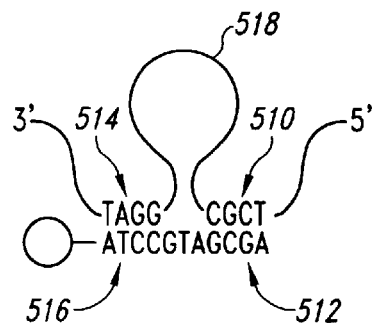
Figure 5C:
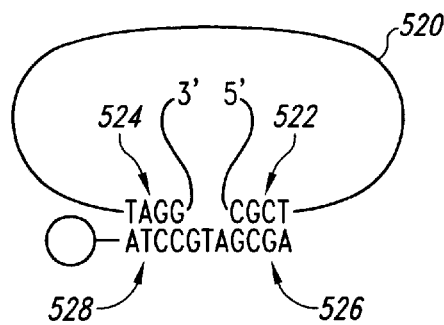
Figure 6:
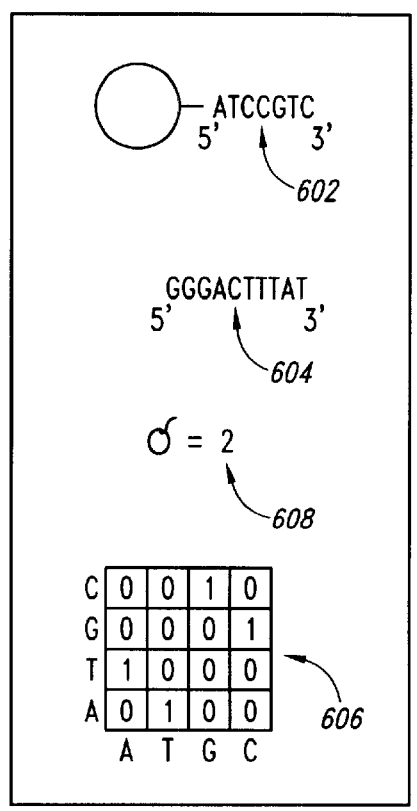
FIG. 6 illustrates the input to a high-level pseudo-code implementation of one embodiment of the present invention.

FIG. 6 illustrates the input to the high-level pseudo-code implementation. The input includes the subunit sequence of a probe molecule, declared as ProbSeq on line 3 of the above pseudo-code and illustrated as probe sequence 602 in FIG. 6. The probe sequence has a subunit length of lp, as declared above on line 3. In the example input shown in FIG. 6, lp has the value 7. The input also includes a target sequence, declared as TarSeq above on line 4, with length lt, illustrated as target sequence 604 in FIG. 6. In the example illustrated in FIG. 6, lt has the value 10. It should be noted that, in practical applications, probe sequences may often include 20 to 30 subunits and target sequences may include up to many thousands of subunits.

Input to the high-level pseudo-code implementation also includes a matrix indicating stability values for all possible pairs of subunits, in this case deoxyribonucleotides, declared above as Stab, on line 5, and illustrated as matrix 606 in FIG. 6. A number of different possible approaches to obtaining stability values are possible. The present example is based on a simple WC base pairing model, or symbolic string model, in which a WC base pairing between a probe nucleotide subunit and a target nucleotide subunit is arbitrarily assigned the value "1" and all other non-WC and anti-WC base pairings are assigned the value "0." However, more complex thermodynamic considerations may be applied to calculating stabilities, such as calculations of the contributions of different possible nucleotide pairings to denaturation, or melting temperature $T_m$, or to the free energy of non-covalent bonding $\Delta G$. A final input parameter is a stability threshold for a single fragment, declared above on line 8 as σ and illustrated in FIG. 6 by equation 608. In the present example, illustrated in FIG. 6, the stability threshold is a minimum length for contiguous WC base pairs within a substring sequence fragment, in the example illustrated in FIG. 6, the value "2." Thus, in the present example, a fragment comprises at least two adjacent WC base pairs between the probe molecule and the target molecule.

The output from the high-level pseudo-code implementation consists of a list of hybridization paths, declared below:

```
1    Output:
2
3        pathList    -a list of fragmented hybridization paths and
4                    their symbolic or thermodynamic scores.
```

Figure 7:
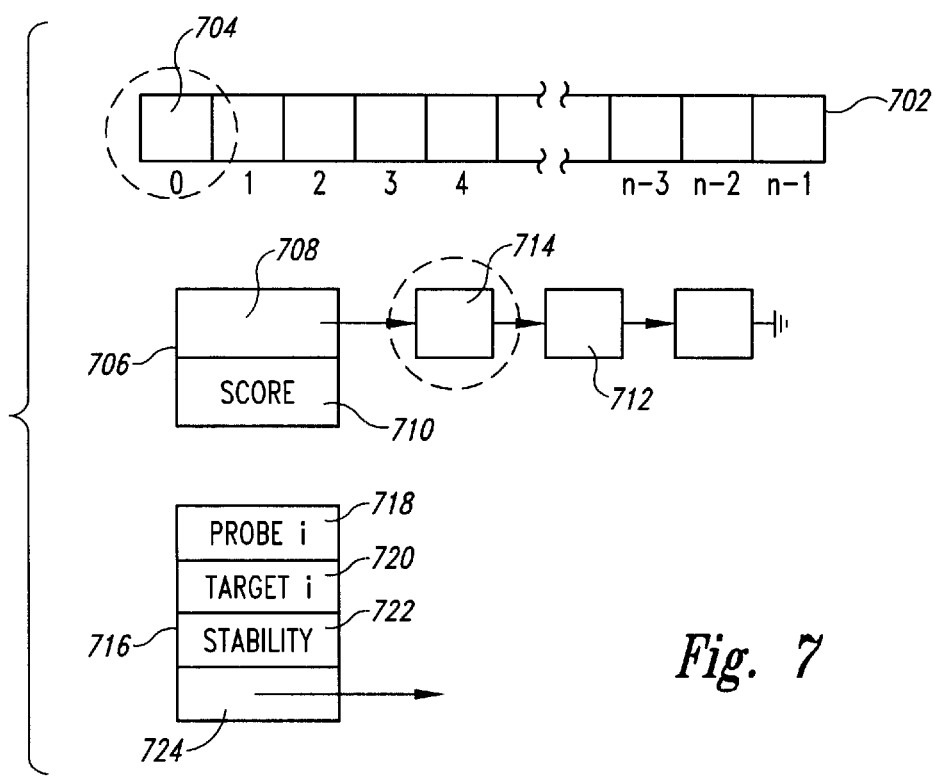
FIG. 7 shows an example implementation of a path list.

FIG. 7 shows an example implementation of the path list pathList. A path list is an array 702 of path descriptors, such as path descriptor 704. The path descriptors within the array have index values 0 through n−1, where n is the number of path descriptors in the list. A path descriptor 706 includes two fields: (1) a pointer to a fragment list 708; and (2) a score 710. The score 710 represents a calculated stability for the single-fragment or multi-fragment hybridization represented by the path descriptor 706. The list of fragments 712 referenced by the path descriptor field 708 is a linked list of one or more fragment descriptors, such as fragment descriptor 714. A fragment descriptor 716 includes four fields: (1) "probe i," the sequence number or index of the first subunit in 5'-3' order of the probe subsequence of the fragment within the probe sequence 718; (2) "target i," the index of the first nucleotide of the subsequence of the target molecule, in 3'-5' order, of the fragment within the target molecule sequence 720; (3) "stability," a calculated stability of hybridization for the fragment 722; and (4) a reference to the next fragment descriptor in a list of fragment descriptors 724. In alternative embodiments, as, for example, embodiments employing a thermodynamic model rather than symbolic base-pair matching, in which the stability of a fragment is not equal to the fragment's length, an additional length field may be included in each fragment descriptor.

The present high-level pseudo-code implementation employs a number of internal variables and data structures, declared below:

```
1    Internal Variables and Data Structures:
2
3    H              -a probe/target interaction matrix
4    fragList       -a list of fragments
5    G              -a matrix representation of a graph, with fragment
6                   indices and edges between a pair of fragments (i,
7                   j) represented by the value "1" in the matrix
                    cell G(i, j)
8    i, j, k, l     -sequence numbers of nucleotides within
     sequences
9    f, g,          -sequence numbers of fragments in fragList
10   fragStab       -fragment stability
11   newPaths       -local path list
12   π              -a path
13   CurrPathList   -a path list parameter
14   CurrPathLength -length of path lists being constructed
15   MaxPathLength  -constant maximum path length to be considered
16   tFragSeqList   -a local list of fragment sequence numbers
```

Figure 8:
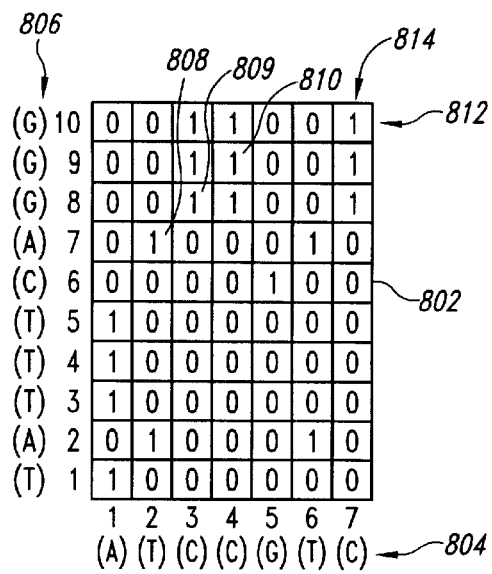
FIG. 8 shows a representative probe/target interaction matrix.

A probe/target interaction matrix is declared as H above, on line 3. A representative probe/target interaction matrix is shown in FIG. 8. The indices, or sequence numbers, of the nucleotide subunits of the probe sequence, written in 5'-3' order, serve as the column indices 804 of the probe/target interaction matrix 802. The indices of the nucleotide subunits within the target sequence, written in 3'-5' order, serve as row indices 806 of the probe/target interaction matrix. A cell of the probe/target interaction matrix represents the stability, taken from the stability matrix 606 of FIG. 6, for the interaction between the probe subunit having the index corresponding to the column of the cell and the target subunit having the index corresponding to the row of the cell. For example, an association between the second subunit T of the probe molecule and the 7$^{th}$ (in 3'-5' order) subunit A of the target molecule, a WC base pair, is represented by the value "1" in the cell with indices (7, 2) 808 in the probe/target interaction matrix 802. In the present implementation, fragments are indicated in the probe/target interaction matrix by ascending diagonal sequences of cells all containing the value "1." For example, starting with cell 808 having indices (7,2), there is an ascending diagonal sequence of cells 808–810 having the value "1" with indices (7,2), (8,3), and (9,4). This represents subsequence complementarity between the probe subsequence TCC representing subunits 2–4 in 5'–3' order within the probe molecule and target subsequence AGG representing subunits 7–9 in 3'–5' order. This target subsequence can also be written in 5'–3' order as GGA. Again, as discussed above in the background section, hybridization between DNA polymers requires the polymers to be antiparallel with respect to one another; thus probe subsequences are considered in 5'–3' order while complementary target sequences are considered in 3'–5' order.

Figure 9:
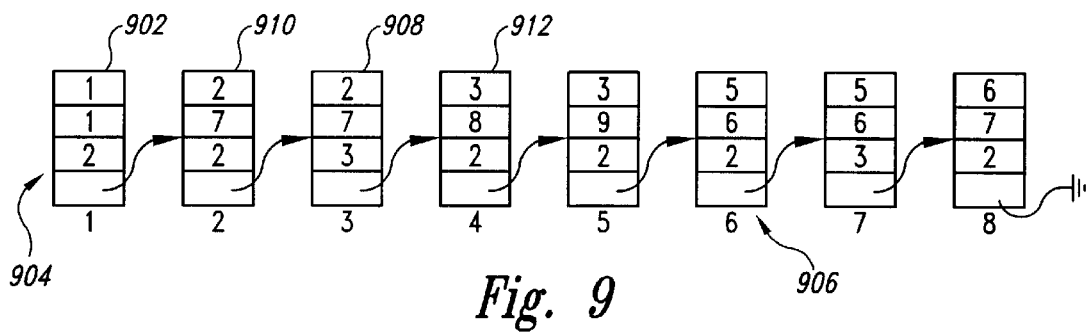
FIG. 9 shows an example implementation of fragList obtained from analysis of the probe/target interaction matrix shown in FIG. 8.

The high-level pseudo-code implementation employs a list of fragments fragList that lists all possible fragments having consecutive WC base pairs obtained through analysis of the probe/target interaction matrix. FIG. 9 shows an example implementation of fragList obtained from analysis of the probe/target interaction matrix shown in FIG. 8. Each fragment descriptor in fragList, such as fragment descriptor 902, contains the same fields as the fragment descriptor 716 shown in FIG. 7. A temporary list of fragments, tFragSeqList, is additionally used in the routine assemble discussed below.

Figure 10:
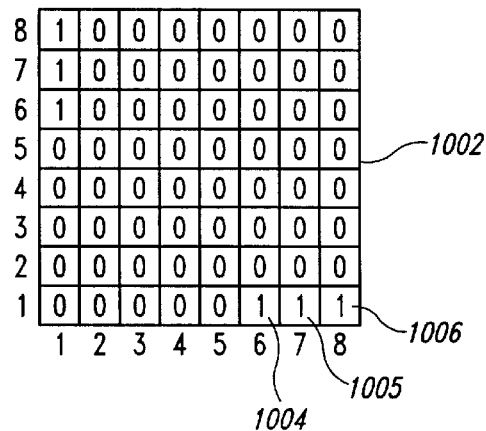
FIG. 10 shows a computational representation of the graph "G."

The high-level pseudo-code implementation employs a matrix representation of a graph, declared above as G on line 5, to indicate possible pairs of fragments that may be interconnected by loops in one or more of the probe and target molecules. Representative loops are shown and discussed with reference to FIGS. 5B and 5C above. Vertices in the graph are fragments from fragList, shown in FIG. 9. Edges in the graph interconnecting two fragments indicate that the two fragments are non-overlapping and that chemically-reasonable loop-forming polymer sequences in the probe and target molecules interconnect the fragments, allowing the two fragments to simultaneously occur as a two-fragment hybridization with intervening loop regions. A computational representation of the graph G is shown in FIG. 10. The graph is represented by matrix 1002. Each cell in the matrix corresponds to a pair of fragments, or vertices. A cell containing the value "0" indicates that no edge occurs between the vertices, and a value "1" in the cell indicates that the graph contains an edge between two vertices. For example, cell 1004 having indices (1,6) indicates that the fragments having sequence numbers 1 and 6 (904 and 906 in FIG. 9) can simultaneously occur within the probe and target molecules having sequences ProbeSeq and TarSeq, respectively, to create a two-fragment hybridization between probe molecule 602 and target molecule 604.

The high-level pseudo-code implementation employs the variables i, j, k, and l, as indexes of nucleotides within the probe and target molecule sequences. The variables f and g, declared above on line 9, are used to represent the sequence numbers, or indices, of fragments within the fragment list fragList. The variable fragStab, declared above on line 10, contains a fragment stability that is calculated for a fragment. The variable newPaths, declared above on line 11, is a local pathList similar to the output parameter pathList, described above. The variable π, declared above on line 12, represents a path, as described by a path descriptor such as path descriptor 706 in FIG. 7. The parameter CurrPathList, declared above on line 13, is a path list of the same form as the output parameter pathList described in FIG. 7, and is used as a parameter for a recursive routine, described below. The parameter CurrPathLength, declared above on line 14, is an integer variable containing the length of the path list CurrPathList. Finally, the constant MaxPathLength, declared above on line 15, is the maximum path length, or, in other words, a maximum number of fragments, to be considered for combination as multi-fragment cross hybridization, or, in other words, the maximum length, in fragments, of a multi-fragment hybridization.

The routine init, provided below, fills in the values of the probe/target interaction matrix H by considering all possible pairwise interactions between one subunit of the probe molecule and a second subunit of the target molecule:

```
1   init
2
3   for j = 1 to lp
4       for i = 1 to lt
5           H(ij) = Stab(ProbeSeq(j), TarSeq(i))
6       endfor
7   endfor
```

The routine init contains two nested for-loops which together produce the indices (i,j) of every cell in the probe/target interaction matrix (802 in FIG. 8) representing all possible pairwise interactions between probe and target subunits, and the values for the cells are calculated on line 5, above, by using the identity of the subunits at the ith position in the target molecule and the jth position in the probe molecule as indices for a cell in the Stab matrix (606 in FIG. 6) indicating the stability values for all possible subunit-type pairings. Note that the probe/target interaction matrix will vary in size depending on the lengths of the probe and target sequences. Also note that, rather than abstracting stability values from the Stab matrix (606 in FIG. 6), more complex thermodynamic calculations may be used to calculate a stability based on melting temperature or ΔG of attractive interaction.

The routine findFrags, which analyzes the probe/target interaction matrix in order to discover all possible complementary subsequences having contiguous stabilizing subunit interactions, or fragments, is provided below:

```
1   findFrags
2
3   fragList = Ø
4   for i = 1 to (lp - 1)
5       for j = 1 to(lt - 1)
6           fragStab = 0
7           k = i
8           l = j
9           while WC(ProbeSeq(k), TarSeq(l))
10              fragStab = fragStab + H(k,l)
11              if fragStab ≥ σ
12                  add(i, j, fragStab, fragList)
13              endif
14              k = k + 1
15              l = l + 1
16          endwhile
17      endfor
18  endfor
```

In the above implementation of the routine "findFrags," it is assumed that a fragment must consist of at least two contiguous stabilizing subunit interactions or, in other words, the fragment must have at least length 2. Thus, as discussed above, since fragments are represented in the probe/target interaction matrix as ascending diagonal sequences of cells having the value "1," valid fragments may not start from either the top row (812 in FIG. 8) or the final column (814 in FIG. 8) of the probe/target interaction matrix. Therefore, only cells having row indices between 1 and lt−1 and column indices between 1 and lp−1 need be considered as possible starting points for fragments. Thus, the nested for-loops comprising lines 4–81 generate indices within the above-described range of indices for all possible cells of the probe/target interaction matrix that may serve as starting points of ascending diagonals of cells having length greater than or equal to 2 and containing the value "1." The list of fragments fragList is initialized, on line 3, to be null. Lines 6–16 are executed, in whole or in part, for each potential starting point for a fragment. First, an accumulator fragStab is initialized to contain the value "0" on line 6. This accumulator will accumulate a total combined stability for all subunit interactions within the fragment. Next, local variables k and l are set to the values of variables i and j, respectively, on lines 7 and 8. The while-loop comprising lines 9–16 attempts to follow an ascending diagonal of cells within the probe/target interaction matrix which all contain the value "1." The while-loop tests that the probe and target nucleotides at positions k and l form a WC base pair. When this condition is true, indices k and l are incremented on lines 14 and 15 so that the next ascending diagonal cell to the current cell is considered in the next iteration of the while-loop comprising lines 9–16. Termination of the while-loop occurs either when a non-WC base pair is encountered, and the while-loop test fails on line 9, or when no more nucleotides remain in either or both of the probe or target sequences, in which case either or both function calls ProbeSeq(k) and TarSeq(l) return values that cause the while-loop test to fail. On line 10, the local variable fragStab is incremented by the stability of the subunit pairing currently considered in the current iteration of the while-loop, found in the probe/interaction matrix cell having indices (l,k). If the current value of variable fragStab is greater than or equal to the stability threshold σ, as detected on line 11, then the fragment represented by the ascending diagonal starting at probe/interaction matrix cell (i,j) with length k−i+1 and stability fragStab is added to the list fragList on line 12.

It should be noted that, on line 10, fragStab is calculated by adding stabilities of each base pair within a fragment. As noted above, these stabilities are, in turn, obtained from the matrix H, the values for which are, in turn, determined from fixed stability values stored in the matrix Stab. As further noted above, more complex thermodynamic calculations may be used to calculate stabilities based on, for example, melting temperature, ΔG of attractive interaction, and other thermodynamic considerations. Moreover, the calculation of overall stability of a fragment may involve non-additive or non-linear combinations of base-pair stabilities. The method of calculating stabilities shown above in findFrags, is merely an example of one of an almost limitless number of ways in which overall fragment stabilities may be calculated. Moreover, stabilities may depend on other molecules and ions present in the experimental environment, and accurate calculations of stabilities may therefore require additional parameters.

FIG. 9 shows the contents of the fragment list fragList resulting from execution of the routine findFrags using the probe/target interaction matrix shown in FIG. 8 and the probe and target molecules described in FIG. 6. Consider the ascending diagonal in FIG. 8 beginning at cell 808 and ending at cell 819 in FIG. 10. That ascending diagonal represents a three-base-pair fragment described by fragment descriptor 908 in FIG. 9. However, there are two additional subfragments contained within that fragment, namely the subfragment comprising cells 808 and 809 represented by fragment descriptor 910 in FIG. 9 and the subfragment comprising cells 809 and 810 represented by fragment descriptor 912 in FIG. 9. The subfragment described by fragment descriptor 910 is found first by the routine findFrags when i and j have values 2 and 7, respectively, k and j have values 3 and 8, respectively, and the local variable fragStab has value 2, following the increment operation on line 10, above. In the next iteration of the while-loop comprising lines 9–16, the fragment described by fragment descriptor 908 is found. Finally, in a subsequent iteration of the outer nested loops that begin on lines 4 and 5, above, when i and j have the values 3 and 8, respectively, the fragment represented by fragment descriptor 912 is found. Thus, the routine findFrags finds all possible fragments having fragment stabilities greater than a threshold stability a that can be obtained by any possible anti-parallel overlapping of the probe and target molecule sequences.

The routine generateGraph, provided below, generates the values of the matrix G (1002 in FIG. 10) representing a graph with edges indicating pairwise compatibility of fragments within multi-fragment hybridizations:

```
1  generateGraph
2
3  for all f,g ∈ sequence numbers of fragments in fragList
4      if testLoop(fragList(f), fragList(g)) set G(f,g) = 1
5      else set G(f,g) = 0
6      endif
7  endfor
```

The routine generateGraph considers all possible pairs of fragments in the list fragList and calls the subroutine testLoop on line 4 to determine whether the fragments may simultaneously hybridize to form a multi-fragment cross hybridization between the probe and target molecules. Many different types of criteria can be used by testLoop to determine whether two fragments are compatible within a two-fragment cross-hybridization. For example, intervening loops between the fragment sequences of the probe and target molecules may be required to have minimum and possibly maximum lengths, and more complex considerations may attempt conformational analysis of the probe and target molecules to determine whether it is likely that the complementary sequences of the two fragments may become positioned in solution relative to one another in order to create local regions of double-stranded DNA.

The routine assemble is a recursive routine that identifies all possible single-fragment and multi-fragment hybridizations, or paths, by analyzing the list fragList:

```
1  pathList = assemble(CurrPathList, CurrPathLength, MaxPathLength)
2
3  if CurrPathLength = 0
4      CurrPathList = single vertex paths created from all fragments in fragList
5      CurrPathLength = 1
```

-continued

```
6       pathList = assemble(CurrPath List, CurrPathLength, MaxPathLength)
7    else if CurrPathLength = MaxPathLength
8       pathList = CurrPathList
9    else
10      newPaths = Ø
11      for all paths π ∈ CurrPathList
12         for all g ∉ the sequence numbers of the fragments in π
13            if (G(f,g) == 1) for all f ∈ the sequence numbers of fragments in π
14               add(g, tFragSeqList)
15         endfor
16         for all g ∈ tFragSeqList
17            if (π + fragList(g) ∉ newPaths) add(π + fragList(g), newPaths)
18         endfor
19      endfor
20      if (newPaths == Ø) pathList = CurrPathList
21      else
22         CurrPathList = CurrPathList ∪ newPaths
23         CurrPathLength = CurrPathLength + 1
24         pathList = assemble(CurrPathList, CurrPathLength, MaxPathLength)
25      endif
26   endif
```

Figure 11:
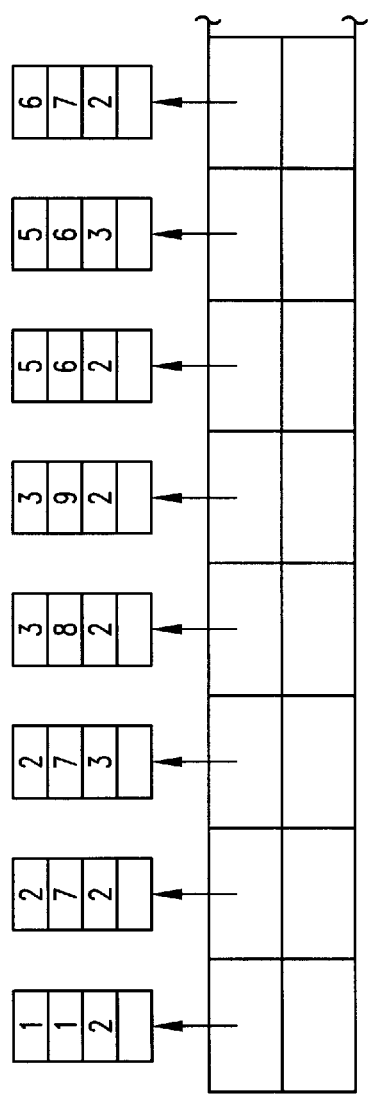
FIG. 11 illustrates the contents of CurrPathList following the first invocation of the routine assemble.

The routine assemble returns a completed patlList on line 1, above, and takes three parameters: (1) CurrPathList, a current path list representing the contents of the path list of the recursive invocation of the routine "assemble" that calls the current invocation of the routine assemble; (2) CurrPathLength, the number of path descriptors in Curr-PathList; and (3) MaxPathLength, the largest number of fragments that may be included in a multi-fragment path. The routine assemble is first called with a null CurrPathList having a CurrPathLength equal to 0. In the first call to the routine assemble, CurrPathList is created by creating path descriptors each describing single-fragment hybridizations represented by each of the fragment descriptors in the fragment list fragList on line 4, above. FIG. 11 illustrates the contents of CurrPathList following the first invocation of the routine assemble. CurrPathLength is updated on line 5, and the routine assemble is recursively called on line 6 in order to find multi-fragment paths. If the routine assemble is invoked with a CurrPathLength parameter already at the maximum allowable length, as detected on line 7, then the routine assemble returns the supplied parameter CurrPath-List as a result on line 8, causing all previous recursive invocations of the routine assemble to similarly return CurrPathList from the deepest recursive call to the routine assemble. If the routine assemble is invoked with a non-null CurrPathList parameter and a CurrPathLength parameter less than MaxPathLength, then lines 10–22 may be executed. On line 10, a local path list newPaths is initialized to be null. On lines 11–19, new paths having lengths one greater than any previous path in CurrPathList are constructed from paths already resident in CurrPathList by adding to each current path all possible additional single fragments from the fragment list fragList. Addition of fragments to current paths is possible only when an edge exists in the graph represented by matrix G indicating that the fragment to be added and the fragments currently within the path are compatible, as detected on line 13. In addition, on line 17, before adding a path to newPaths, the routine assemble determines whether the path is already in newPaths, and only adds a path to newPaths if the path is not already in newPaths. Alternatively, this test might be omitted and redundant paths filtered out at a later stage, e.g. in the routine scoreAndSort.

Figure 12:
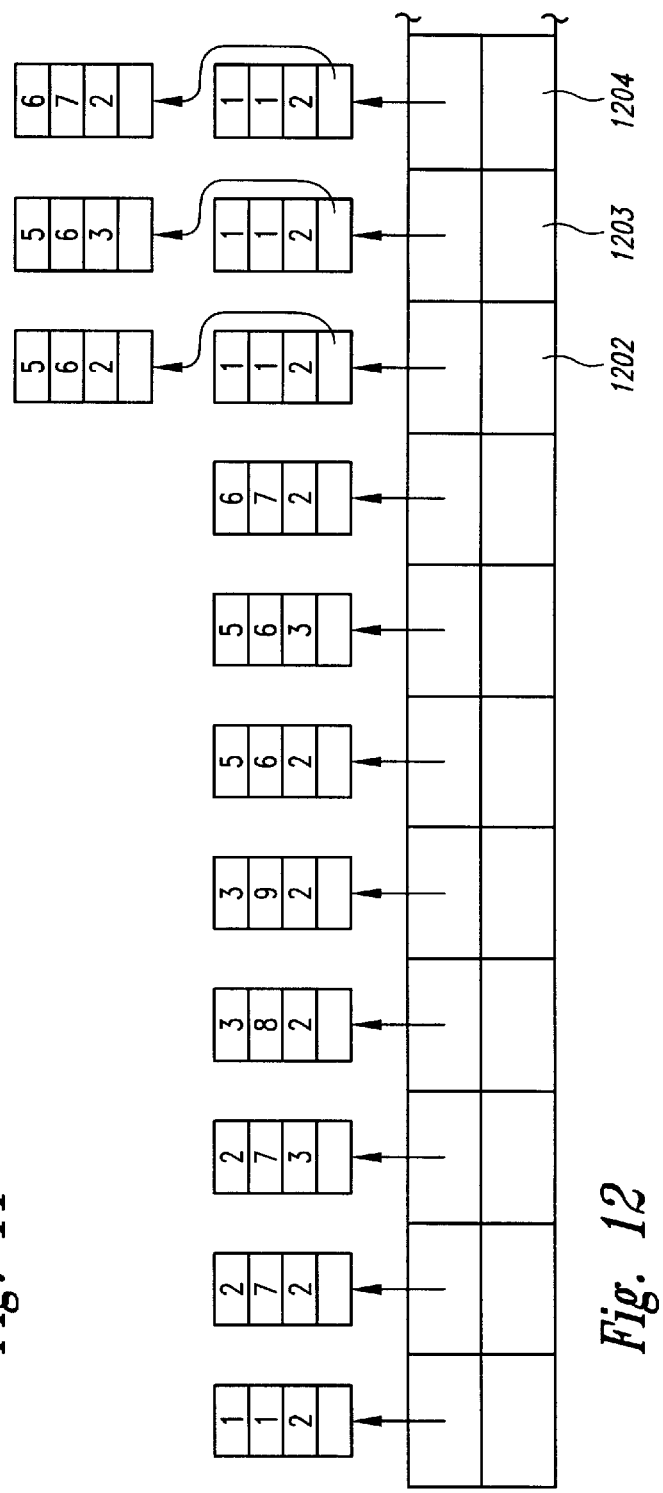
FIG. 12 shows the contents of CurrPathList following execution of lines 11–16 of the routine assemble during the second invocation of the routine assemble.

FIG. 12 shows the contents of CurrPathList following execution of lines 11–16 during the second invocation of the routine assemble. The three edges 1004–1006 in FIG. 10 indicate that two-fragment multi-fragment cross-hybridization is possible with the fragment pairs 1 and 6, 1 and 7, and 1 and 8, respectively. The three two-fragment multi-fragment hybridizations are represented in FIG. 12 by path descriptors 1202–1204, respectively. If no new paths are found in an invocation of the routine assemble, as detected on line 20, then no additional multi-fragment paths can be found, and the routine assemble returns CurrPathList as a result. Otherwise, CurrPathList is updated to include all new paths found on lines 10–16, CurrPathLength is incremented on line 23, and the routine assemble is recursively invoked on line 24 with the new values of the parameters CurrPathList and CurrPathLength.

Figure 13:
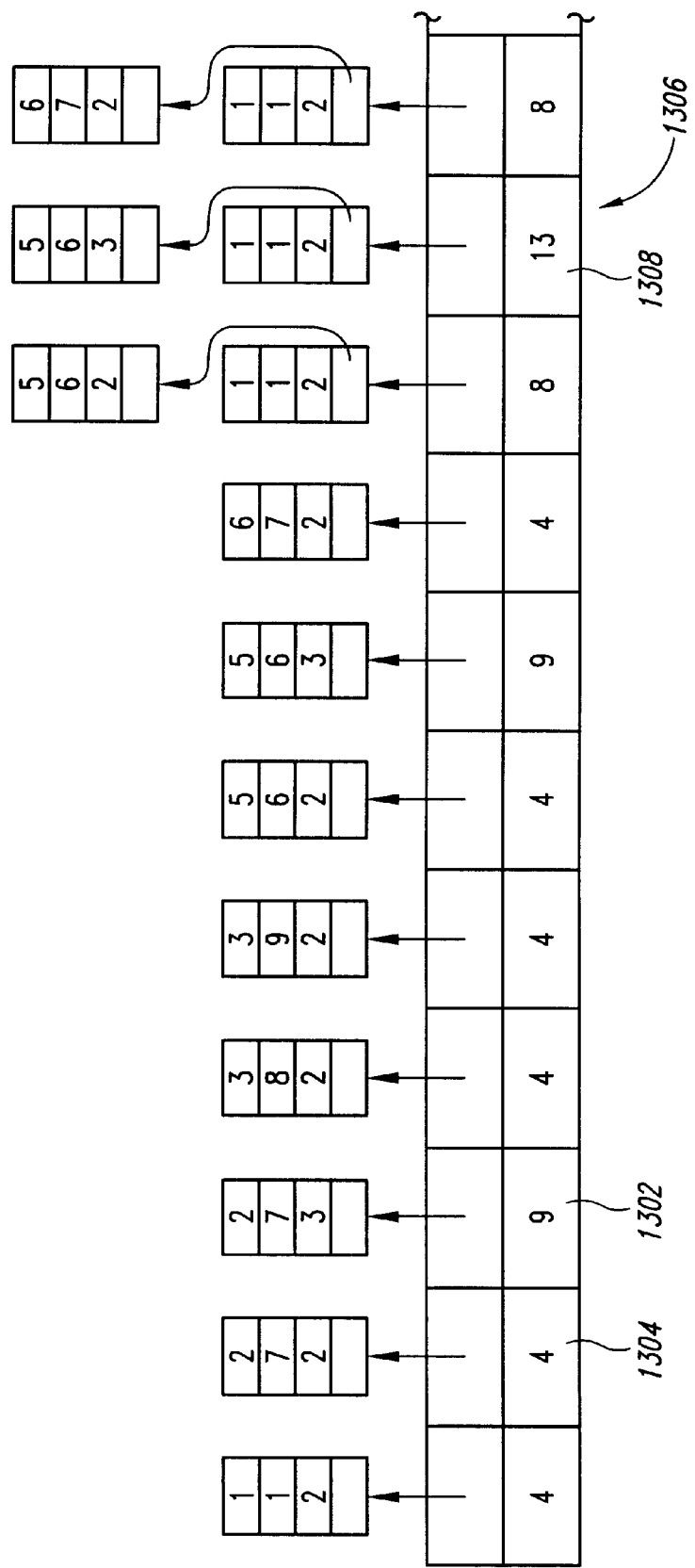
FIG. 13 shows the list "pathList" following calculation of scores and prior to sorting.

The routine scoreAndSort calculates scores for each path in the path list returned by the routine assemble and sorts the path list in descending order of calculated scores. FIG. 13 shows the list pathList following calculation of scores and prior to sorting. There are many different approaches to calculating hybridization stabilities, or scores, for paths. In one approach, the score for a multi-fragment path may be calculated as the sum of the scores of each fragment within the multi-fragment path. However, in order to emphasize the increased hybridization stability arising from longer-length fragments, nonlinear combined score calculation may be employed according to the formula:

$$\text{score} = \sum_{i=1}^{n} S_i^x$$

where n is the number of fragments in a path, $S_i$ is the score for a particular fragment in the path, and x is some real number greater than 1. By using a non-linear combination of scores, longer length and more stable fragments contribute significantly more to the overall score than shorter, or less stable fragments. In the current example, the stability of a fragment is equal to the number of subunits of the fragment, and the term "x" in the above equation is 2. Thus, as can be seen in FIG. 13, single-fragment hybridization of length 3 results in a score of 9, such as score 1302, while a single-fragment hybridization of length 2 results in a score of only 4, such as score 1304. If there were a single fragment of length 4 in this example, it would have a score of 16. However, a two-fragment hybridization including fragments of length 3 and 2, represented in FIG. 13 by path descriptor 1306, produces a score of 13 (1308 in FIG. 13). Thus, longer single-fragment hybridizations are greatly preferred to shorter single-fragment hybridizations and are often preferred to multi-fragment hybridizations in which the maximum length of any fragment is less than the length of the longer single-fragment hybridization, but multi-fragment hybridizations including at least one fragment of length n are preferred to single-fragment hybridizations of length n. It should be noted that more complex scoring methodologies may be employed to take into account the structure of intervening loops, using methods similar to those used to evaluate the conformational stabilities of single-stranded RNA, and to take into account probabilities of solution conformations that lead to the complementary regions of a first fragment, separated by a loop from a second fragment, coming together in close proximity to one another following hybridization of the second fragment. The above calculation is merely one example of many possible approaches to scoring hybridizations. On line 6 of the routine scoreAndSort, above, the path list pathList may be sorted so that the most stable hybridizations can easily be found at the top or beginning of Pathlist.

Finally, the routine main calls the above-described routines in the order in which they are discussed, above, to return a possibly truncated list of the highest potential hybridizations between a probe and target molecule:

```
1    main
2
3        init
4        findFrags
5        generateGraph
6        pathList = assemble(Ø, 0, MaxPathLength)
7        scoreAndSort
8        return top(pathList)
```

Again, as described above, the program presented by the above-described high-level pseudo-code implementation may be called repeatedly to evaluate a probe molecule for hybridization potential with many different possible sample molecules, and the program may be called multiple times for multiple potential probe molecules in order to select probe molecules for an application with high hybridization potentials for desired target molecules and low hybridization potentials for undesirable molecules to which the probe molecule may be exposed during the application.

Alternative embodiments of the present invention may use nearest neighbor thermodynamic calculations to assess fragment stabilities, rather than the simple symbolic matching described in the above embodiment. In one such alternative embodiment, two matrices DeltaG and I replace the matrix H in the above embodiment. The matrix I contains the initial free energy of formation of all possible probe/target base pairs, calculated from matrices IH and IS that contain the enthalpy and entropy of formation of all possible probe/target base pairs according to the matrix equation:

$$I=IH-T*IS$$

where T is the temperature of the solution in which the base pairs form. For DNA/DNA probe/target base pairing, I, IH, and IS have columns and rows corresponding to the deoxynucleotides in the target and probe sequences, in the case of DNA/DNA hybridization. These matrices may be obtained from all possible pair-wise matching of probe and target deoxynucleotides using the probe and target sequences along with 4×4 matrices containing the entropies and enthalpies of base-pair formation for all possible deoxynucleotide pairs. When RNA/DNA, DNA/RNA, and RNA/RNA probe/target hybridization is considered, either three different 4×4 matrices may be employed, or, alternatively, 8×8 matrices with columns and rows corresponding to the deoxynucleotides and nucleotides may be employed.

The matrix DeltaG contains the free energy contribution to hybridization contributed by contiguous pairs of bases. For a sequence of base pairs in a particular fragment, the free energy contribution to hybridization for first base pair of the sequence is obtained from the matrix I, and the free energy contribution of each successive base pair of the sequence following the first base pair is obtained from DeltaG. Matrices DH and DS contain the enthalpy and entropy, respectively, of formation of particular contiguous 2-base-pair sequences. DH and DS may be four-dimensional matrices with indexes corresponding to the four dimensions signifying: (1) the type of nucleotide in the probe molecule in the first base pair of the 2-base-pair sequence; (2) the type of nucleotide in the probe molecule in the second base pair of the 2-base-pair sequence; (3) the type of nucleotide in the target molecule in the first base pair of the 2-base-pair sequence; and (4) the type of nucleotide in the target molecule in the second base pair of the 2-base-pair sequence. Two two-dimensional matrices DeltaH and DeltaS may be calculated for a particular probe and target molecule as follows:

$$DeltaS(i,j)=DS[ProbeSeq(j-1), ProbeSeq(j), TarSeq(i-1), TarSeq(i)]$$

$$DeltaH(i,j)=DH[ProbeSeq(j-1), ProbeSeq(j), TarSeq(i-1), TarSeq(i)]$$

Finally, DeltaG is calculated from DeltaS and DeltaH as follows:

$$DeltaG=DeltaH-T*DeltaS$$

It should be noted that the data contained in the matrices DS and DH, as well as the entropies and enthalpies of base pair formation used to calculate I, IH, and IS, are publicly available in the scientific literature. Using the nearest neighbor thermodynamic approach, the routine findFrags may be implemented as follows:

```
1    findFrags
2
3    fragList = Ø
4    for i = 1 to (lp - 1)
5        for j = 1 to (lt - 1)
6            fragStab = -I(i,j)
7            k = i + 1
8            l = j + 1
9            while -DeltaG(k,l) > σ₁
10               fragStab = fragStab -DeltaG(k,l)
11               if fragStab ≧ σ₂
12                   add(i, j, fragStab, (k - 1 + 1), fragList)
13               endif
14               k = k + 1
15               l = l + 1
16           endwhile
17       endfor
18   endfor
``` where $\sigma_1$ is a minimal free energy contribution of a subsequent base pair of a sequence, $\sigma_2$ is a minimal free energy of formation of a fragment, and the length of a fragment is provided as an argument to the function add for an additional length field in the fragment descriptor, as discussed above.

C++-Like Pseudo-code Implementation

The following, rather extensive C++-like pseudo-code implementation provides an alternative embodiment of the present invention. Three C++-like classes are employed to encapsulate the concepts of nucleotide base sequence, fragment, and path as described above with reference to the first high-level pseudo-code implementation of one embodiment of the present invention. A fourth class encapsulates the calculation of subunit base pair stability based both on the chemical identities of the subunits as well as additional nearest-neighbor considerations. A fifth class is essentially a container for various member functions that are called, in sequence, in a main routine to carry out analysis of probe/target hybridization potential for a probe and target molecule.

First, a number of constants and enumerations are declared that are used throughout the member function implementations described below:

```
1      const int MAX_PROBE_LENGTH = 10;
2      const int MAX_TARGET_LENGTH = 100;
3      const int MAX_FRAGMENTS = 500;
4
5      enum base {A, TU, G, C, X};
6      enum btypes {DNAxDNA, DNAxRNA, RNAxRNA};
7      enum bondType {Anti, WC, nonWC, Unknown};
```

The constant "MAX_PROBE_LENGTH," declared above on line 1, is the maximum length of a probe base sequence that may be considered. This constant, like the following constant "MAX_TARGET_LENGTH," declared above on line 2, serves simply for array bounds in the following pseudo-code. These constants can be adjusted to larger, more realistic values at the expense of increased memory requirements for storing various arrays. Alternatively, memory space for arrays may be allocated dynamically during program execution in order to decrease or largely eliminate static memory requirements for the program. The enumeration "base," declared above on line 5, provides symbolic codes for the identities of the different possible bases. The current implementation allows for DNA and RNA probe and target molecules. The base value "TU" stands for either thymidine or uridine, depending upon whether the polymer in which the base resides is a DNA polymer or an RNA polymer, respectively. The value "X" indicates a subunit with undetermined identity. The enumeration "btypes," declared above on line 6, includes three different values indicating whether both the target and probe are DNA polymers, whether one of the target and probe is an RNA polymer and the other of the target and probe is a DNA polymer, or whether both target and probe are RNA polymers. The enumeration "bondType," declared above on line 7, indicates the nature of a considered base pair, the values for which include, as discussed above in a previous section: (1) "Anti," indicating a purine-purine or pyrimidine-pyrimidine base pair; (2) "WC," indicating a Watson-Crick base pair; (3) "nonWC," indicating an AC or GT base pair; and (4) "Unknown," indicating that the nature of one or both of the bases in the base pair is unknown.

The class "sequence," shown below encapsulates a DNA or RNA polymer base sequence:

```
1    classsequence
2    {
3        private:
4            bool      DNA;
5            int len;
6            base      seq[MAX_TARGET_LENGTH];
7            char      cseq[MAX_TARGET_LENGTH + 1];
8
9        public:
10           base      operator [](int i);
11           int   length();
12           bool      getDNA();
13           base      getBase(int i);
14           void copy(sequence* s);
15           char      getChar(int i);
16           sequence(bool dnaSeq, char* Seq);
17           sequence();
18           ~sequence();
19   };
```

An instantiation of the class sequence represents either a probe or target DNA or RNA sequence. The class sequence contains the following data members: (1) "DNA," a Boolean value indicating whether or not a sequence is a DNA sequence; (2) "len," the length of the sequence; (3) "seq," an array holding a representation of the sequence as an ordered set of values of the enum "base;" and (4) "cseq," an array containing character representations of the bases of the sequence. It is assumed that the maximal length of the target sequence is greater than the maximal length of the probe sequence, and thus the constant "MAX_TARGET_LENGTH" is used to define the lengths of the arrays so that an instance of the class sequence can accommodate either a probe or a target sequence. The class sequence includes the following member functions: (1) "operator[ ]" an array-type operator that returns the enum base representation of the base at index "i" within the sequence; (2) "length," that returns the length, in bases, of the sequence; (3) "getDNA," a member function that returns the current value of the data member "DNA;" (4) "getBase," a member function that returns the enum base value of the base having sequence number "i" within the sequence; (5) "copy," a member function that copies the sequence supplied as argument "s" into the current sequence; (6) "getChar," a member function that returns the character representation of the base at sequence number "i" within the sequence; and (7) two constructors and a destructor, declared above on lines 16–18. Implementations for these member functions are not provided, as they are simple functions easily constructed by one skilled in the art.

The class "fragment," provided below represents a sub-sequence of the probe molecule and a complementary sub-sequence of the target molecule that can hybridize together to form a region of double-stranded polymer:

```
1    class fragment
2    {
3        private:
4            int       I;
5            int       J;
6            int       len;
7            fragment*      next;
8            int       score;
9            int       ident;
10
11       public:
12           int       firstI();
13           int       lastI();
14           int       firstJ();
15           int       lastJ();
16           fragment*      getNext();
17           void  setNext(fragment* frag);
18           int       getScore();
19           int       getID();
20           int       getLength();
21           fragment(int i, int j, int length, int scor, int id);
22           ~fragment();
23   };
```

The class fragment contains the following data members: (1) "I," the index or sequence number of the first base of the probe sequence in the fragment; (2) "J," the sequence number or index of the first base of the target subsequence portion of the fragment; (3) "len," the length of the fragment, in base pairs; (4) "next," a pointer to a next fragment; (5) "score," the hybridization potential calculated for the fragment; and (6) "ident," a numerical identifier that identifies the fragment. Note that, in the current implementation, both target and probe sequences are maintained in 5'-3' order. To avoid converting target sequences to 3'-5' order, diagonals representing fragments in the target/probe interaction matrix are descending, rather than ascending. The class "fragment" includes the following member functions: (1) "firstI," that returns the sequence number of the first base of the fragment in the probe sequence; (2) "lastI," that returns the sequence number of the last base of the fragment in the probe sequence; (3) "firstJ," that returns the sequence number, or index, of the first base of the fragment in the target sequence; (4) "lastJ," that returns the sequence number of the last base of the fragment in the target sequence; (5) "getNext," that returns a pointer, or reference, to the next instance of the class "fragment" in a linked list of fragments; (6) "setNext," that sets the value of the data member "next;" (7) "getScore," that returns the value of a data member "score;" (8) "getID," that returns the value of the data member "ident;" (9) "getLength," that returns the length of the fragment; and (10) a constructor and destructor, declared above on lines 21 and 22. Implementation of the member functions of the class "fragment" are not provided, as they are quite routine and easily written by one skilled in the art of programming.

The class "path," provided below, represents a single-fragment or multi-fragment hybridization, similar to the path descriptor described above with reference to FIG. 7:

```
1   class path
2   {
3       private:
4           fragment* first;
5           fragment* last;
6           fragment* nxt;
7           int score;
8           int num;
9
10      public:
11          int         getScore();
12          void        setScore(int scor);
13          fragment*       getFirst();
14          fragment*       getNext();
15          void        addToFront(fragment* p);
16          void        addToRear(fragment* p);
17          void        print(sequence *probe, sequence* target);
18          path* copy();
19          path(fragment* p);
20          ~path();
21  };
```

The class "path" contains the following data members: (1) "first," a reference to the first fragment in the list of fragments of the path; (2) "last," a reference to the last fragment of the path; (3) "next," a data member used for tracking the next fragment to return during calls to member function "getNext" described below; (4) "score," the nonlinear score for the path comprising fragments within a fragment list referenced by the data member "first;" and (5) "num," the number of fragments in the path represented by the fragment list referenced by the data member "first," having the value 1 for a single-fragment path and a value greater than 1 for a multi-fragment path. The class "path" contains the following member functions: (1) "getScore," that returns the value of the data member "score;" (2) "setScore," that sets the data member "score" to the value of the supplied parameter "scor;" (3) "getFirst," that returns a pointer to the first fragment of the path; (4) "getNext," that returns the next fragment of the path, repeatably callable in order to traverse the entire fragment list referenced by data member "first;" (5) "addToFront," a member function that adds an instance of the class "fragment" describing a fragment referenced by parameter "p" to the head of the fragment list pointed to by data member "first," updating the data member "score" to reflect the addition of the fragment; (6) "addToRear," similar to the above-described member function "addToFront" except that the fragment referenced by the parameter "p" is added to the end of the fragment list; (7) "print," a member function that prints out a representation of the path to an output device; (8) "copy," a member function that allocates a new instance of the class "path," copies the data and fragment list of the current path to the new instance of the class "path," and returns a reference to the new instance of the class "path;" and (9) a constructor and destructor declared above on lines 19 and 20. In the current implementation, the power to which fragment scores are raised in the nonlinear total score calculation ("x" in the equation discussed above in the previous subsection) is "2."

The class "baseToBaseInteraction," provided below, represents calculation of the stability of a base pair, one base of which is provided by the probe molecule and a second base of which is provided by the target molecule:

```
1   class path
2   {
3       private:
4           fragment* first;
5           fragment* last;
6           fragment* nxt;
7           int score;
8           int num;
9
10      public:
11          int         getScore();
12          void        setScore(int scor);
13          fragment*       getFirst();
14          fragment*       getNext();
15          void        addToFront(fragment* p);
16          void        addToRear(fragment* p);
17          void        print(sequence *probe, sequence* target);
18          path* copy();
19          path(fragment* p);
20          ~path();
21  };
```

The class "baseToBaseInteraction" includes three array data members "DNA_DNA," "RNA_RNA," and "RNA_DNA" that contain initial stability values for each possible base pairing between DNA polymers, RNA polymers, or an RNA and a DNA polymer, respectively. These arrays are similar to the array Stab (606 in FIG. 6) described with reference to the previous implementation. The class "baseToBaseInteraction" includes the following member functions: (1) "interaction," that returns a value of the enum bond type that indicates the basic type of interaction, Anti, WC, or non-WC, for the bases supplied as parameters "b1" and "b2;" (2) "baseToBaseBondStrength," a member function that calculates a final stability value for a base pair formed from the base with sequence number "i" in the probe sequence "probe" and a base having sequence number "j" in the target sequence "target," where the DNA or RNA nature of the two bases is indicated by the parameter "bt;" and (3) a constructor and destructor declared above on lines 12 and 13. Implementation of the member function "interaction" is straightforward, and produces values of the above-described enum bond type according to the description in the Background section, above. A detailed implementation of the member function "baseToBaseBondStrength" is provided below:

```
1    int baseToBaseInteraction::baseToBaseBondStrength (sequence* probe, sequence*target,
2                                    btypes bt, int i, int j)
3    {
4        bondType prev = Unknown;
5        bondType cur = Unknown;
6        bondType nxt = Unknown;
7        int prevI = i - 1;
8        int prevJ = j + 1;
9        int nxtI = i + 1;
10       int nxtJ = j - 1;
11
12       if (prevI >= 0 && prevJ < target->length())
13           prev = interaction(probe->getBase(prevI), target->getBase(prevJ));
14       if (nxtI < probe->length() && nxtJ >= 0)
15           nxt = interaction(probe->getBase(nxtI), target->getBase(nxtJ));
16       cur = interaction(probe->getBase(i), target->getBase(j));
17       if (cur == nonWC)
18       {
19           if ((prev == nonWC && (nxt == WC || nxt == nonWC)) ||
20               (prev == WC && nxt == nonWC))
21           {
22               if (bt == DNAxDNA)
23                   return DNA_DNA[probe->getBase(i)][target->getBase(j)];
24               else if (bt == DNAxRNA)
25                   return RNA_DNA[probe->getBase(i)][target->getBase(j)];
26               else return RNA_RNA[probe->getBase(i)][target->getBase(j)];
27           }
28           else return 0;
29       }
30       else if (cur == Anti) return 0;
31       else if (cur = WC)
32       {
33           if ((prev == Anti && nxt != WC) ||
34               (prev == nonWC && nxt != WC)) return 0;
35           else
36           {
37               if (bt == DNAxDNA)
38                   return DNA_DNA[probe->getBase(i)][target->getBase(j)];
39               else if (bt == DNAxRNA)
40                   return RNA_DNA[probe->getBase(i)][target->getBase(j)];
41               else return RNA_RNA[probe->getBase(i)][target->getBase(j)];
42           }
43       }
44       else return 0;
45   }
```

The above member function uses a nearest-neighbor approach to calculate base pair stabilities based both on inherent stabilities arising from the identity of the two bases of the base pair, as stored in the data member matrices of the class "baseToBaseInteraction," described above, and also based on the stabilities of the previous and subsequent base pairs in a fragment. The theory is that the stability of neighboring base pairs contributes to the stability of a given base pair in a more or less cooperative fashion. On lines 12–16, the bond types of the previous, subsequent, and the currently considered base pair are determined. If the currently considered base pair is a non-WC base pair, as determined on line 17, then the stability for the base pair is calculated on lines 19–28. If, on the other hand, the currently considered base pair has bond type "Anti," as determined on line 30, then a value of 0 is returned for the stability of the base pair, regardless of the types of base pairs preceding and subsequent to the currently considered base pair. If the currently considered base pair is a WC base pair, as detected on line 31, then the stability of the currently considered base pair is calculated and returned on lines 33–44.

The values of the data member matrices of the class "baseToBaseInteraction" are set within the constructor for the class, a partial implementation with respect to data member "DNA_DNA" is provided below:

```
baseToBaseInteraction::baseToBaseInteraction()
{
    DNA_DNA[A][A] = 0;
    DNA_DNA[A][G] = 0;
    DNA_DNA[A][C] = 1;
    DNA_DNA[A][TU] = 2;
    DNA_DNA[G][A] = 0;
    DNA_DNA[G][G] = 0;
    DNA_DNA[G][C] = 4;
    DNA_DNA[G][TU] = 1;
    DNA_DNA[C][A] = 1;
    DNA_DNA[C][G] = 4;
    DNA_DNA[C][C] = 0;
    DNA_DNA[C][TU] = 0;
    DNA_DNA[TU][A] = 2;
    DNA_DNA[TU][G] = 1;
```

-continued

```
        DNA_DNA[TU][C] = 0;
        DNA_DNA[TU][TU] = 0;
}
```

The class "probeHybrid," provided below, is essentially a container for a number of member functions that sequentially determine a list of paths representing possible hybridizations between a probe and target molecule, analogous to the path list returned by the high-level pseudo-code implementation described in the previous subsection:

```
1  class probeHybrid
2  {
3        private:
4              sequence target;
5              sequence probe;
6              int hyb_matrix[MAX_PROBE_LENGTH]
                             [MAX_TARGET_LENGTH];
7              bool         loopMatrix[MAX_FRAGMENTS]
                             [MAX_FRAGMENTS];
8              path*        paths[MAX_TARGET_LENGTH *
                             MAX_PROBE_LENGTH];
9              baseToBaseInteraction b2bInter;
10             int    totalScore;
11             path*         topTen[10];
12             int    topNum;
13             int    topLow;
14             btypes bt;
15             int    num;
16             bool          targSupplied;
17
18             void generateHyb_matrix();
19             bool findNxtFragInDiag(int & i, int & j);
20             void findSingleFragPaths();
21             bool loop(fragment* f1, fragment* f2);
22             void topTenInsert(path* p);
23
24      public;
25             int    score (sequence* prob);
26             void print();
27             void newTarget (sequence* targ);
28             probeHybrid(sequence* targ);
29             probeHybrid();
30             virtual ~probeHybrid();
31 };
```

The class "probeHybrid" includes the following data members: (1) "target," the sequence of a target molecule; (2) "probe," the sequence of a probe molecule; (3) "hyb_matrix," a probe/target interaction matrix similar to matrix "H" in the high-level pseudo-code implementation discussed above in the previous subsection; (4) "loopMatrix," a matrix similar to the matrix "G" describing a graph in the high-level pseudo-code implementation provided above in the first subsection; (5) "paths," a path list representing the possible hybridizations between the probe and target sequences; (6) "b2bInter," an instance of the class "baseToBaseInteraction," discussed above; (7) "totalScore," a total score representing the cumulative scores of all hybridizations represented by instances of the class "path" in the above-described path list "path;" (8) "topTen," a partial path list including the ten paths having the highest scores; (9) "topNum" and "topLow," variables used in computing the partial patlList "topTen," described above; (10) "bt," an indication of whether the probe and target hybridization is a DNA to DNA, DNA to RNA, or RNA to RNA hybridization; (11) "num," the number of paths currently contained in the path list "paths;" and (12) "targSupplied," an indication of whether a target is currently referenced by data member "target." The class "probeHybrid" contains the following private member functions: (1) "generateHyb_matrix," a member function equivalent to the function init of the high-level pseudo-code implementation described in the previous subsection; (2) "findNxtFragInDiag," a member function that starts from a particular cell in the Hyb_matrix and finds a next fragment; (3) "findSingleFragPaths," a member function equivalent to the function findFrags of the high-level pseudo-code implementation described in the previous subsection; (4) "loop," a member function equivalent to the function generateGraph of the high-level pseudo-code implementation described in the previous subsection; and (5) "topTenInsert," a member function that inserts a newly created path into the partial pathList "topTen" if its score warrants inclusion in the list of topTen paths. The class "probeHybrid" includes the following public member functions: (1) "score," a member function that accepts a reference to a probe sequence "probe" and computes the hybridization potential for the probe sequence to the target sequence referenced by data member "target;" (2) "print," a member function that prints out the partial path list "topTen;" (3) "newTarget," a member function that places a new target sequence into the data member "target;" and (4) two constructors and a destructor, declared above on lines 28–30.

Implementations of the member functions of class "probeHybrid" are provided below. As these are full implementations, details of operation of these member functions are best discerned directly from the implementations, along with the above descriptions of the various classes employed in the implementation, and so commentary on these implementations will be rather more concise than the descriptions provided for the routines of the high-level pseudo-code implementation described in the previous subsection.

An implementation for the member function "generateHyb_matrix" is provided below:

```
1  void probeHybrid::generateHyb_matrix()
2  {
3        btypes bt;
4        int i, j;
5
6        if (probe.getDNA() && target.getDNA()) bt = DNAxDNA;
7        else if (probe.getDNA() || target.getDNA()) bt = RNAxRNA;
8        else bt = DNAxRNA;
9
10       for (i = 0; i < probe.length(); i++)
11             for (j = 0; j < target.length(); j++)
12                    hyb_matrix[i][j] =
13                           b2binter.baseToBaseBondStrength
                                  (&probe, &target, bt, i, j);
14 }
```

This member function uses a nested for-loop in lines 10–13 to calculate all possible base pair interactions between the probe and target molecules and stores the value in the matrix "hyb_matrix."

An implementation of the member function "findNxtFragInDiag" is provided below:

```
1  bool probeHybrid::findNxtFragInDiag(int & i, int & j)
2  {
3        int si, sj, size;
4        fragment* f;
5        path* p;
```

-continued

```
6       int nxtSc;
7       int scor;
8
9       if (i >= probe.length() || j < 0) return false;
10      while (hyb_matrix[i][j] == 0)
11      {
12          i++;
13          j--;
14          if (i >= probe.length() || j < 0) break;
15      }
16      if (i < probe.length() - 1 && j > 0)
17      {
18          si = i;
19          sj = j;
20          size = 1;
21          scor = hyb_matrix[i][j];
22
23          while (true)
24          {
25              i++;
26              j--;
27              if ((i >= probe.length()) ||
28                  (j < 0) ||
29                  ((nxtSc = hyb_matrix[i][j]) == 0))
                    break;
30              size++;
31              scor += nxtSc;
32          }
33          if (size > 2)
34          {
35              f = new fragment(si, sj, size, scor, num);
36              p = new path(f);
37              topTenInsert(p);
38              totalScore += p->getScore();
39              path[num++] = p;
40          }
41          return true;
42      }
43      else return false;
44  }
```

This member function is provided with indices of a cell of the matrix "hyb_matrix" and, starting from that cell, attempts to find the next single fragment in a descending diagonal path. The fragment must, in the current implementation, have a size greater than two and must consist of base pairs having non-zero entries in the probe/target interaction matrix "hyb_matrix." A newly found fragment generates a new single-fragment path that is potentially included in the partial path list "topTen" on line 37 and included in the comprehensive path list "paths" on line 39.

An implementation of the member function "findSingleFragPaths" is provided below:

```
1   void probeHybrid::findSingleFragPaths()
2   {
3       int i, j, ii, jj;
4
5       generateHyb_matrix();
6       for (j = 1; j < target.length(); j++)
7       {
8           ii = 0;
9           jj = j;
10          while (true)
11          {
12              if (!findNxtFragInDiag(ii, jj)) break;
13          }
14      }
15      for (i = 1; i < (probe.length() - 1); i++)
16      {
17          ii = i;
18          jj = target.length() - 1;
19          while (true)
20          {
21              if (!findNxtFragInDiag(ii, jj)) break;
22          }
23      }
24  }
```

This member function begins searching on descending diagonals emanating from the top-most row and left-most columns of the probe/target interaction matrix "hyb_matrix." The fragments in each diagonal are found by repeated calls to the member function "findNxtFragInDiag."

An implementation of the member function "loop" is provided below:

```
1   bool probeHybrid::loop(fragment* f1, fragment* f2)
2   {
3       int probeLoop, targetLoop;
4
5       if (f1->lastI() < f2->firstI()) // order and no overlap
6       {
7           if (f2->lastJ() > f1->firstJ())
8           {
9               //delta loop
10              probeLoop = f2->firstI() - f1->lastI();
11              targetLoop = f2->lastJ() - f1->firstJ();
12              if (probeLoop > 3 && targetLoop > 15)
                    return true;
13              else return false;
14          }
15          else if (f1->lastJ() > f2->firstJ())
16          {
17              // omega
18              probeLoop = f2->firstI() - f1->lastI();
19              targetLoop = f1->lastJ() - f2->firstJ();
20              if ((probeLoop > 2 && targetLoop > 5) ||
21                  (probeLoop == targetLoop)) return true;
22              else return false;
23          }
24          else return false;
25      }
26      else return false;
27  }
```

This member function determines whether a fragment referenced by the first parameter "f1" and a fragment referenced by the second parameter "f2" can coexist in a multi-fragment cross-hybridization between the probe and target molecules. This routine generally decides whether intervening sequences, between the fragments "f1" and "f2," of the probe and target molecules meet certain length constraints or whether the two fragments are simply joined by a stretch of mismatched base pairs, or in other words, joined by a loop with equal-length sequences.

```
10
11      if (!targSupplied) return 0;
12      totalScore = 0;
13      num = 0
14      topNum = 0;
15      probe.copy(prob);
16      findSingleFragPaths();
17
18      for (i = 0; i < num; i++)
19          for (j = 0; j < num; j++)
20          {
21              loopMatrix[i][j] = loop(paths[i]->
                    getFirst(), paths[j]->getFirst());
```

```
22              }
23
24       multipleFragPaths = num;
25       while (true)
26       {
27              f = 0;
28              thisIteration = num;
29              while (f < multipleFragPaths)
30              {
31                     for (p = highwater; p < thisIteration; p++)
32                     {
33                            if (loopMatrix[paths[f]->getFirst()->
                                   getID()]
34                                   [paths[p]->getFirst()->
                                          getID()])
35                            {
36                                   npat = paths[p]->copy();
37                                   frag = new fragment(paths[f]->
                                          getFirst()->firstI(),
38                                                 paths[f]->
                                                        getFirst()->
                                                        firstJ(),
39                                                 paths[f]->
                                                        getFirst()->
                                                        getLength(),
40                                                 paths[f]->
                                                        getFirst()->
                                                        getScore(),
41                                                 paths[f]->
                                                        getFirst()->
                                                        getID());
42                                   npat->addToFront(frag);
43                                   paths[num++] = npat;
44                                   totalScore += npat->getScore();
45                                   topTenInsert(npat);
46                            }
47                     }
48                     f++;
49              }
50              if (num == thisIteration) break;
51              highwater = thisIteration;
52       }
53       return totalScore;
54 }
```

On lines 18–22, the member function score calculates all values contained in the above-described matrix "loopMatrix." Next, the member function "score" calculates possible multi-fragment paths and adds the multi-fragment paths to the pathList "paths," and, An implementation of the member function "topTenInsert" is provided below, without further discussion:

```
void probeHybrid::topTenInsert(path* p)
{
    int i, j;
    if (topNum == 0)
    {
        topLow = p->getScore();
        topNum = 1;
        topTen[0] = p;
    }
    else if (topNum < 10)
    {
        i = 0;
        while (i < topNum && p->getScore() < topTen[i]->
            getScore()) i++;
        if (i != topNum)
        {
            for (j = topNum; j > i; j--) topTen[j] = topTen[j-1];
        }
        topTen[i] = p;
        topLow = topTen[topNum]->getScore();
        topNum++;
    }
    else if (p->getScore() > topLow)
    {
        i = 0;
        while (i < 10 && p->getScore() < topTen[i]->getScore())
            i++;
        if (i == 10) return;
        for (j = topNum - 1; j > i; j--) topTen[j] = topTen[j-1];
        topTen[i] = p;
        topLow = topTen[9]->getScore();
    }
}
```

An implementation of the member function "score" is provided below:

```
1  int probeHybrid::score (sequence* prob)
2  {
3         int multipleFragPaths;
4         int highwater = 0;
5         int thisIteration;
6         int f, p;
7         path* npat;
8         fragment* frag;
9         int i, j;
``` when warranted, to the partial pathList "topTen," in a manner analogous to the calculation of paths in the routine assemble described above in the high-level pseudo-code implementation provided in the previous subsection.

Finally, implementations for the remaining member functions of the class "probeHybrid" and a main routine are provided below without further comment:

```
void probeHybrid::newTarget (sequence* targ)
{
    int i;
    for (i = 0; i < num; i++)
        if (paths[i] != NULL) delete (paths[i]);
    target.copy(targ);
    totalScore = 0;
    num = 0;
    topNum = 0;
    targSupplied = true;
}
probeHybrid::probeHybrid(sequence* targ)
{
    targSupplied = true;
    target.copy(targ);
    num = 0;
    totalScore = 0;
    topNum = 0;
}
probeHybrid::probeHybrid()
{
    targSupplied = false;
    num = 0;
    totalScore = 0;
    topNum = 0;
}
probeHybrid::~probeHybrid()
{
    int i;
    for (i = 0; i < num; i++)
        if (paths[i] != NULL) delete (paths[i]);
}
main()
{
    int score;
    sequence probe1(true, "AATTCGCGAGTCG");
```

-continued

```
    sequence target1(true,
     "GCTTATGTAATTCGCGAGTCGAAAATCTTT");
    probeHybrid pH(&target1);
    score = pH.score(&probe1);
    pH.print();
}
```

The top six paths printed by the probeHybrid member function "print" for the probe sequence "AATTCGC-GAGTCG" and target sequence "GCTTATGTAATTCGC-GAGTCGAAAATGTTT" are provided below:

| path 0 | | |
|---|---|---|
| 16 to 11 | | |
| 3 to 8 | | |
| 3'-AGCGCT-5' | | |
| 5'-TCGCGA-3' | | |
| path 1 | | |
| 25 to 23 | 20 to 18 | 16 to 14 |
| 1 to 3 | 6 to 8 | 10 to 12 |
| 3'-TAA-5' | 3'-GCT-5' | 3'-AGC-5' |
| 5'-ATT-3' | 5'-CGA-3' | 5'-TCG-3' |
| path 2 | | |
| 20 to 18 | 16 to 14 | |
| 6 to 8 | 10 to 12 | |
| 3'-GCT-5' | 3'-AGC-5' | |
| 5'-CGA-3' | 5'-TCG-3' | |
| path 3 | | |
| 22 to 19 | | |
| 2 to 15 | | |
| 3'-AAGC-5' | | |
| 5'-TTCG-3' | | |
| path 4 | | |
| 25 to 23 | 16 to 14 | |
| 1 to 3 | 10 to 12 | |
| 3'-TAA-5' | 3'-AGC-5' | |
| 5'-ATT-3' | 5'-TCG-3' | |
| path 5 | | |
| 25 to 23 | 20 to 18 | |
| 1 to 3 | 6 to 8 | |
| 3'-TAA-5' | 3'-GCT-5' | |
| 5'-ATT-3' | 5'-CGA-3' | |

This data was generated by execution of a full implementation of the C++-like pseudo-code implementation provided above, where the probe and target sequences can be observed in the fifth and sixth lines of the routine "main."

Although the present invention has been described in terms of a particular embodiment, it is not intended that the invention be limited to this embodiment. Modifications within the spirit of the invention will be apparent to those skilled in the art. For example, many different types of thermodynamic and structural chemistry stability analyses can be employed to estimate the stabilities of probe/target base pairs and fragments and the chemical reasonability of loops joining fragments in multi-fragment hybridizations. As pointed out above, an almost limitless number of different implementations of the present invention are possible, depending on the programming language or languages employed, programming styles, data structures, and hybridization models. Although DNA/DNA interactions were prominent in the above implementations, alternative embodiments of the present invention can predict hybridization potentials for many different types of naturally occurring and synthetic polymers.

The foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed, obviously many modifications and variations are possible in view of the above teachings. The embodiments were chosen and described in order to best explain the principles of the invention and its practical applications and to thereby enable others skilled in the art to best utilize the invention and various embodiments with various modifications as are suited to the particular use contemplated.

SEQUENCE LISTING

```
<160> NUMBER OF SEQ ID NOS: 11

<210> SEQ ID NO 1
<211> LENGTH: 4
<212> TYPE: DNA
<213> ORGANISM: Artificial Sequence
<220> FEATURE:
<223> OTHER INFORMATION: A hypothetical sequence

<400> SEQUENCE: 1 atcg                                                                       4

<210> SEQ ID NO 2
<211> LENGTH: 11
<212> TYPE: DNA
<213> ORGANISM: Artificial Sequence
<220> FEATURE:
```

```
<223> OTHER INFORMATION: A hypothetical target sequence

<400> SEQUENCE: 2
tcgctacgga t                                                    11

<210> SEQ ID NO 3
<211> LENGTH: 5
<212> TYPE: DNA
<213> ORGANISM: Artificial Sequence
<220> FEATURE:
<223> OTHER INFORMATION: A hypothetical target subsequence

<400> SEQUENCE: 3 cgcta                                                            5

<210> SEQ ID NO 4
<211> LENGTH: 5
<212> TYPE: DNA
<213> ORGANISM: Artificial Sequence
<220> FEATURE:
<223> OTHER INFORMATION: A hypothetical probe subsequence

<400> SEQUENCE: 4 tagcg                                                            5

<210> SEQ ID NO 5
<211> LENGTH: 11
<212> TYPE: DNA
<213> ORGANISM: Artificial Sequence
<220> FEATURE:
<223> OTHER INFORMATION: A hypothetical probe sequence

<400> SEQUENCE: 5
atccgtagcg a                                                    11

<210> SEQ ID NO 6
<211> LENGTH: 4
<212> TYPE: DNA
<213> ORGANISM: Artificial Sequence
<220> FEATURE:
<223> OTHER INFORMATION: A hypothetical target subsequence

<400> SEQUENCE: 6 tcgc                                                             4

<210> SEQ ID NO 7
<211> LENGTH: 4
<212> TYPE: DNA
<213> ORGANISM: Artificial Sequence
<220> FEATURE:
<223> OTHER INFORMATION: A hypothetical probe subsequence

<400> SEQUENCE: 7 gcga                                                             4

<210> SEQ ID NO 8
<211> LENGTH: 4
<212> TYPE: DNA
<213> ORGANISM: Artificial Sequence
<220> FEATURE:
<223> OTHER INFORMATION: A hypothetical target subsequence

<400> SEQUENCE: 8 ggat                                                             4
```

-continued

```
<210> SEQ ID NO 9
<211> LENGTH: 4
<212> TYPE: DNA
<213> ORGANISM: Artificial Sequence
<220> FEATURE:
<223> OTHER INFORMATION: A hypothetical probe subsequence

<400> SEQUENCE: 9 atcc                                                                    4

<210> SEQ ID NO 10
<211> LENGTH: 7
<212> TYPE: DNA
<213> ORGANISM: Artificial Sequence
<220> FEATURE:
<223> OTHER INFORMATION: A hypothetical probe sequence

<400> SEQUENCE: 10 atccgtc                                                                 7

<210> SEQ ID NO 11
<211> LENGTH: 10
<212> TYPE: DNA
<213> ORGANISM: Artificial Sequence
<220> FEATURE:
<223> OTHER INFORMATION: A hypothetical target sequence

<400> SEQUENCE: 11
gggactttat                                                             10
```

It is intended that the scope of the invention be defined by the following claims and their equivalents:

What is claimed is:

1. A method for predicting the hybridization potential between a probe polymer and a target polymer, the method comprising:

predicting and storing stabilities of pairing between pairs of subunits, one subunit of the pair in a sequence of probe subunits that together compose the probe polymer, and a second subunit of the pair in a sequence of target subunits that together compose the target polymer;

analyzing the stabilities of pairing between pairs of subunits to enumerate possible fragments, each fragment comprising a probe subunit subsequence and a target subunit subsequence that may pair together in a stable association;

considering all possible pairs of fragments to determine pairs of fragments that may occur concurrently in the probe and target polymers to form different types of two-fragment hybridizations, including two-fragment hybridizations in which the two fragments are separated by intervening, non-hybridized sequences of different lengths in the target and probe polymers; and enumerating possible full-length, single-fragment, and multi-fragment hybridizations.

2. The method of claim 1 wherein the probe polymer is a DNA polymer and the target polymer is a DNA polymer.

3. The method of claim 1 wherein the probe polymer is a DNA polymer and the target polymer is an RNA polymer.

4. The method of claim 1 wherein the probe polymer is an RNA polymer and the target polymer is a DNA polymer.

5. The method of claim 1 wherein the probe polymer is an RNA polymer and the target polymer is an RNA polymer.

6. The method of claim 1 wherein the probe and target polymers are selected from among:

DNA polymers;

RNA polymers;

protein polymers;

hybrid biopolymers; and synthetic polymers, including synthetic nucleotide polymers.

7. The method of claim 1 wherein the stabilities of pairing between pairs of subunits are predicted by thermodynamic considerations.

8. The method of claim 1 wherein the stabilities of pairing between pairs of subunits are predicted by symbolic matching of subunits and retrieval of stability values predetermined for each possible pair of symbols representing polymer subunits.

9. The method of claim 1 wherein the stabilities of pairing between pairs of subunits are predicted by symbolic matching of subunits and retrieval of stability values predetermined for each possible pair of symbols representing polymer subunits and by consideration of stabilities of nearest-neighbor subunit pairs.

10. The method of claim 1 wherein the stabilities of pairing between pairs of subunits are predicted by thermodynamic considerations and by consideration of stabilities of nearest-neighbor subunit pairs.

11. The method of claim 1 wherein the predicted stabilities of pairing between pairs of subunits are stored in a probe/target interaction matrix comprising rows and columns of values, each value indexed by:

a position of the probe subunit of the pair of subunits corresponding to the value; and a position of the target subunit of the pair of subunits corresponding to the value.

12. The method of claim 11 wherein analyzing the stabilities of pairing between pairs of subunits to enumerate possible fragments further includes:
considering initial values within the probe/target interaction matrix, and for each initial value, adding to a list of possible fragments any consecutive diagonal sequences of values that conform to threshold stability requirements emanating from the initial value.

13. The method of claim 12 wherein the threshold stability requirements include a length of fragment requirement.

14. The method of claim 12 wherein the threshold stability requirements include a threshold stability value calculated from the stabilities of subunit pairings that together compose the fragment.

15. The method of claim 1 wherein considering possible pairs of fragments to determine pairs of fragments that may occur concurrently in the probe and target polymers to form a two-fragment hybridization further includes considering all possible fragment pairs, storing an indication that a fragment pair may occur concurrently in the probe and target polymers when the subsequences composing the fragments are separated by unpaired sequences within the probe and target polymers meeting minimum and maximum length requirements.

16. The method of claim 1 wherein considering possible pairs of fragments to determine pairs of fragments that may occur concurrently in the probe and target polymers to form a two-fragment hybridization further includes considering all possible fragment pairs, storing an indication that a fragment pair may occur concurrently in the probe and target polymers when a calculation of the thermodynamic and configurational stability of a two-fragment hybridization comprising the fragment pair meets a threshold stability requirement.

17. The method of claim 1 wherein considering possible pairs of fragments to determine pairs of fragments that may occur concurrently in the probe and target polymers to form a two-fragment hybridization further includes storing indications of the pairs of fragments that may occur concurrently in the probe and target polymers within a representation of a graph having fragment vertices, with edges representing pairs of fragments that may occur concurrently in the probe and target polymers.

18. The method of claim 1 wherein enumerating possible multi-fragment hybridizations further includes:
initializing a list of possible hybridizations to contain possible single-fragment hybridizations; and
repeatedly selecting each hybridization from the list added in previous iterations and during initialization, and, for each selected hybridization,
selecting each possible single-fragment hybridization,
when the selected single-fragment hybridization and concurrently occur along with the selected hybridization from the list, creating a new multi-fragment hybridization from the selected hybridization and the selected single-fragment hybridization and adding the new multi-fragment hybridization to the list.

19. The method of claim 1 further including:
storing the enumerated possible full-length, single-fragment, and multi-fragment hybridizations in a list of hybridizations.

20. The method of claim 19 further including:
scoring each hybridization in the list of hybridizations for overall stability.

21. The method of claim 20 wherein the score for a hybridization is a sum of scores of all fragments included in the hybridization.

22. The method of claim 20 wherein the score for a hybridization is a sum of scores of all fragments included in the hybridization each raised to a real power.

23. The method of claim 20 wherein the score for a hybridization is a monotonic function of the scores of all fragments included in the hybridization.

24. The method of claim 20 wherein the score for a hybridization is $-\Delta G$, where $\Delta G$ is the free energy of the configuration implied by the hybridization.

25. The method of claim 19 further including:
sorting the list of hybridizations by score.

26. A computer-readable medium storing computer instructions that implement the method of claim 1.

27. Electronic signals embodied in a carrier wave that encodes computer instructions that implement the method of claim 1.

28. A system that predicts the hybridization potential between a probe polymer and a target polymer, the system comprising:
a computer processor;
a computer memory; and
a computer program that takes, as input, a subunit sequence for the probe polymer, a subunit sequence for the target polymer, and a minimum fragment length, and that, by considering all possible pairs of fragments having at least the minimum fragment length to determine pairs of fragments that may occur concurrently in the probe and target polymers to form different types of two-fragment hybridizations, enumerates possible full-length, single-fragment, and multi-fragment hybridizations between the probe polymer and the target polymer in order to predict the hybridization potential between the probe polymer and the target polymer.

29. The system of claim 28 wherein the probe and target polymers are selected from among:
DNA polymers;
RNA polymers;
protein polymers;
hybrid biopolymers; and
synthetic polymers, including synthetic nucleotide polymers.

30. The system of claim 28 wherein the computer program enumerates possible full-length, single-fragment, and multi-fragment hybridizations between the probe polymer and the target polymer by:
predicting and storing stabilities of pairing between pairs of subunits, one subunit of the pair in a sequence of probe subunits that together compose the probe polymer, and a second subunit of the pair in a sequence of target subunits that together compose the target polymer;
analyzing the stabilities of pairing between pairs of subunits to enumerate possible fragments, each fragment comprising a probe subunit subsequence and a target subunit subsequence that may pair together in a stable association;
considering possible pairs of fragments to determine pairs of fragments that may occur concurrently in the probe and target polymers to form different types of two-fragment hybridizations, including two-fragment hybridizations in which the two fragments are separated by intervening, non-hybridized sequences of different lengths in the target and probe polymers; and
combining the enumerated fragments in ways compatible with the determined pairs of fragments that may occur concurrently in the probe and target polymers in order to enumerate possible full-length, single-fragment, and multi-fragment hybridizations.

31. The system of claim 30 wherein the stabilities of pairing between pairs of subunits are predicted by thermodynamic considerations.

32. The system of claim 30 wherein the stabilities of pairing between pairs of subunits are predicted by symbolic matching of subunits and retrieval of stability values predetermined for each possible pair of symbols representing polymer subunits.

33. The system of claim 30 wherein the stabilities of pairing between pairs of subunits are predicted by symbolic matching of subunits and retrieval of stability values predetermined for each possible pair of symbols representing polymer subunits and by consideration of stabilities of nearest-neighbor subunit pairs.

34. The system of claim 30 wherein the stabilities of pairing between pairs of subunits are predicted by thermodynamic considerations and by consideration of stabilities of nearest-neighbor subunit pairs.

35. The system of claim 30 wherein the predicted stabilities of pairing between pairs of subunits are stored in a probe/target interaction matrix comprising rows and columns of values, each value indexed by:
    a position of the probe subunit of the pair of subunits corresponding to the value; and
    a position of the target subunit of the pair of subunits corresponding to the value.

36. The system of claim 35 wherein analyzing the stabilities of pairing between pairs of subunits to enumerate possible fragments further includes:
    considering initial values within the probe/target interaction matrix, and for each initial value, adding to a list of possible fragments any consecutive diagonal sequences of values that conform to threshold stability requirements emanating from the initial value.

37. The system of claim 36 wherein the threshold stability requirements include a length of fragment requirement.

38. The system of claim 36 wherein the threshold stability requirements include a threshold stability value calculated from the stabilities of subunit pairings that together compose the fragment.

39. The system of claim 30 wherein considering possible pairs of fragments to determine pairs of fragments that may occur concurrently in the probe and target polymers to form a two-fragment hybridization further includes considering all possible fragment pairs, storing an indication that a fragment pair may occur concurrently in the probe and target polymers when the subsequences composing the fragments are separated by unpaired sequences within the probe and target polymers meeting minimum and maximum length requirements.

40. The system of claim 30 wherein considering possible pairs of fragments to determine pairs of fragments that may occur concurrently in the probe and target polymers to form a two-fragment hybridization further includes considering all possible fragment pairs, storing an indication that a fragment pair may occur concurrently in the probe and target polymers when a calculation of the thermodynamic and configurational stability of a two-fragment hybridization comprising the fragment pair meets a threshold stability requirement.

41. The system of claim 30 wherein considering possible pairs of fragments to determine pairs of fragments that may occur concurrently in the probe and target polymers to form a two-fragment hybridization further includes storing indications of the pairs of fragments that may occur concurrently in the probe and target polymers within a representation of a graph having fragment vertices, with edges representing pairs of fragments that may occur concurrently in the probe and target polymers.

42. The system of claim 30 wherein enumerating possible multi-fragment hybridizations further includes:
    initializing a list of possible hybridizations to contain possible single-fragment hybridizations; and
    repeatedly selecting each hybridization from the list added in previous iterations of during initialization, and, for each selected hybridization,
    selecting each possible single-fragment hybridization,
    when the selected single-fragment hybridization and concurrently occur along with the selected hybridization from the list, creating a new multi-fragment hybridization from the selected hybridization and the selected single-fragment hybridization and adding the new multi-fragment hybridization to the list.

43. The system of claim 30 further including:
    storing the enumerated possible full-length, single-fragment, and multi-fragment hybridizations in a list of hybridizations.

44. The system of claim 30 further including:
    scoring each hybridization in the list of hybridizations for overall stability.

45. The system of claim 44 wherein the score for a hybridization is a sum of scores of all fragments included in the hybridization.

46. The system of claim 44 wherein the score for a hybridization is a sum of scores of all fragments included in the hybridization each raised to a real power.

47. The system of claim 44 wherein the score for a hybridization is a monotonic function of the scores of all fragments included in the hybridization each raised to a real power.

48. The system of claim 43 further including:
    sorting the list of hybridizations by score.

49. A method for predicting the hybridization potential between a probe polymer and a target polymer, the method comprising:
    predicting and storing stabilities of pairing between pairs of subunits, one subunit of the pair in a sequence of probe subunits that together compose the probe polymer, and a second subunit of the pair in a sequence of target subunits that together compose the target polymer;
    analyzing the stabilities of pairing between pairs of subunits to enumerate possible fragments, each fragment comprising a probe subunit subsequence and a target subunit subsequence that may pair together in a stable association;
    considering possible pairs of fragments to determine pairs of fragments that may occur concurrently in the probe and target polymers to form different types of two-fragment hybridizations, including two-fragment hybridizations in which the two fragments are separated by intervening, non-hybridized sequences of different lengths in the target and probe polymers, by considering all possible fragment pairs, and
    storing an indication that a fragment pair may occur concurrently in the probe and target polymers when a calculation of the thermodynamic and configurational stability of a two-fragment hybridization comprising the fragment pair meets a threshold stability requirement; and enumerating possible full-length, single-fragment, and multi-fragment hybridizations.

50. A method for predicting the hybridization potential between a probe polymer and a target polymer, the method comprising:

predicting and storing stabilities of pairing between pairs of subunits, one subunit of the pair in a sequence of probe subunits that together compose the probe polymer, and a second subunit of the pair in a sequence of target subunits that together compose the target polymer;

analyzing the stabilities of pairing between pairs of subunits to enumerate possible fragments, each fragment comprising a probe subunit subsequence and a target subunit subsequence that may pair together in a stable association;

considering possible pairs of fragments to determine pairs of fragments that may occur concurrently in the probe and target polymers to form different types of two-fragment hybridizations, including two-fragment hybridizations in which the two fragments are separated by intervening, non-hybridized sequences of different lengths in the target and probe polymers, by storing indications of the pairs of fragments that may occur concurrently in the probe and target polymers within a representation of a graph having fragment vertices, with edges representing pairs of fragments that may occur concurrently in the probe and target polymers; and enumerating possible full-length, single-fragment, and multi-fragment hybridizations.

51. The method of claim 1 wherein a probe subunit subsequence and a target subunit subsequence may pair together in a stable association when the probe subunit subsequence and the target subunit subsequence are chemically complementary.

52. The method of claim 1 wherein a probe subunit subsequence and a target subunit subsequence may pair together in a stable association when the probe subunit subsequence and the target subunit subsequence are chemically complementary and have lengths greater than a minimum subsequence length in subunits.

* * * * *